US012564409B2

(12) United States Patent
Maracaja

(10) Patent No.: US 12,564,409 B2
(45) Date of Patent: Mar. 3, 2026

(54) DOUBLE LUMEN AORTIC CANNULA AND CROSS CLAMP ASSEMBLY AND RELATED METHODS

(71) Applicant: Wake Forest University Health Sciences, Winston-Salem, NC (US)

(72) Inventor: Luiz Maracaja, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 386 days.

(21) Appl. No.: 18/042,236

(22) PCT Filed: Aug. 24, 2021

(86) PCT No.: PCT/US2021/047251

§ 371 (c)(1),
(2) Date: Feb. 20, 2023

(87) PCT Pub. No.: WO2022/046702

PCT Pub. Date: Mar. 3, 2022

(65) Prior Publication Data

US 2023/0301661 A1      Sep. 28, 2023

Related U.S. Application Data

(60) Provisional application No. 63/069,799, filed on Aug. 25, 2020.

(51) Int. Cl.
*A61B 17/122* (2006.01)
(52) U.S. Cl.
CPC ..... *A61B 17/122* (2013.01); *A61M 2202/047* (2013.01); *A61M 2210/127* (2013.01)

(58) Field of Classification Search
CPC .......... A61B 17/122; A61M 2202/047; A61M 2210/127; A61M 1/3659; A61M 1/366
See application file for complete search history.

(56) References Cited

U.S. PATENT DOCUMENTS 5,928,253 A    7/1999   Sherman et al.
6,042,563 A    3/2000   Morejohn et al.
(Continued)

OTHER PUBLICATIONS

International Search Report and the Written Opinion of the International Searching Authority corresponding to International Patent Application No. PCT/US2021/047251 (14 pages) (mailed Nov. 8, 2021).

*Primary Examiner* — Brooke Labranche
(74) *Attorney, Agent, or Firm* — Myers Bigel, P.A.

(57) ABSTRACT

Cardiothoracic surgical devices with a dual lumen cannula (8) that cooperates with a clamping assembly (35) for facilitating a CPB. The dual lumen cannula (8) has a distal end portion (8*d*) configured to reside inside an aorta (A) of a patient. The distal end portion (8*d*) has a first lumen (9) and a second lumen (10) in fluid isolation. The first lumen (9) has a lumen orifice (13) that faces a first direction inside the aorta and the second lumen (10) comprises a lumen orifice (15) that faces a second direction that is different than the first direction inside the aorta. The clamp assembly (35) is coupled to the dual lumen cannula (8) and configured with first and second clamp arms (1351, 1352) that are configured to align with the distal end portion (8*d*) of the dual lumen cannula (8) and clamp against opposing external surfaces of a vessel wall of the aorta to compress the vessel wall against the distal end portion (8*d*) of the dual lumen cannula (8) and thereby provide first and second fluidly isolated segments of the aorta.

21 Claims, 35 Drawing Sheets

(56)  References Cited

U.S. PATENT DOCUMENTS

| | | | |
|---|---|---|---|
| 6,726,651 B1 * | 4/2004 | Robinson ......... | A61B 17/12136 |
| | | | 604/4.01 |
| 2003/0208231 A1 | 11/2003 | Williamson et al. | |
| 2005/0222532 A1 * | 10/2005 | Bertolero ............ | A61M 1/3623 |
| | | | 604/102.03 |

* cited by examiner

100′

35s

435

37′

182

181

8h

8d

135m

2351

1351

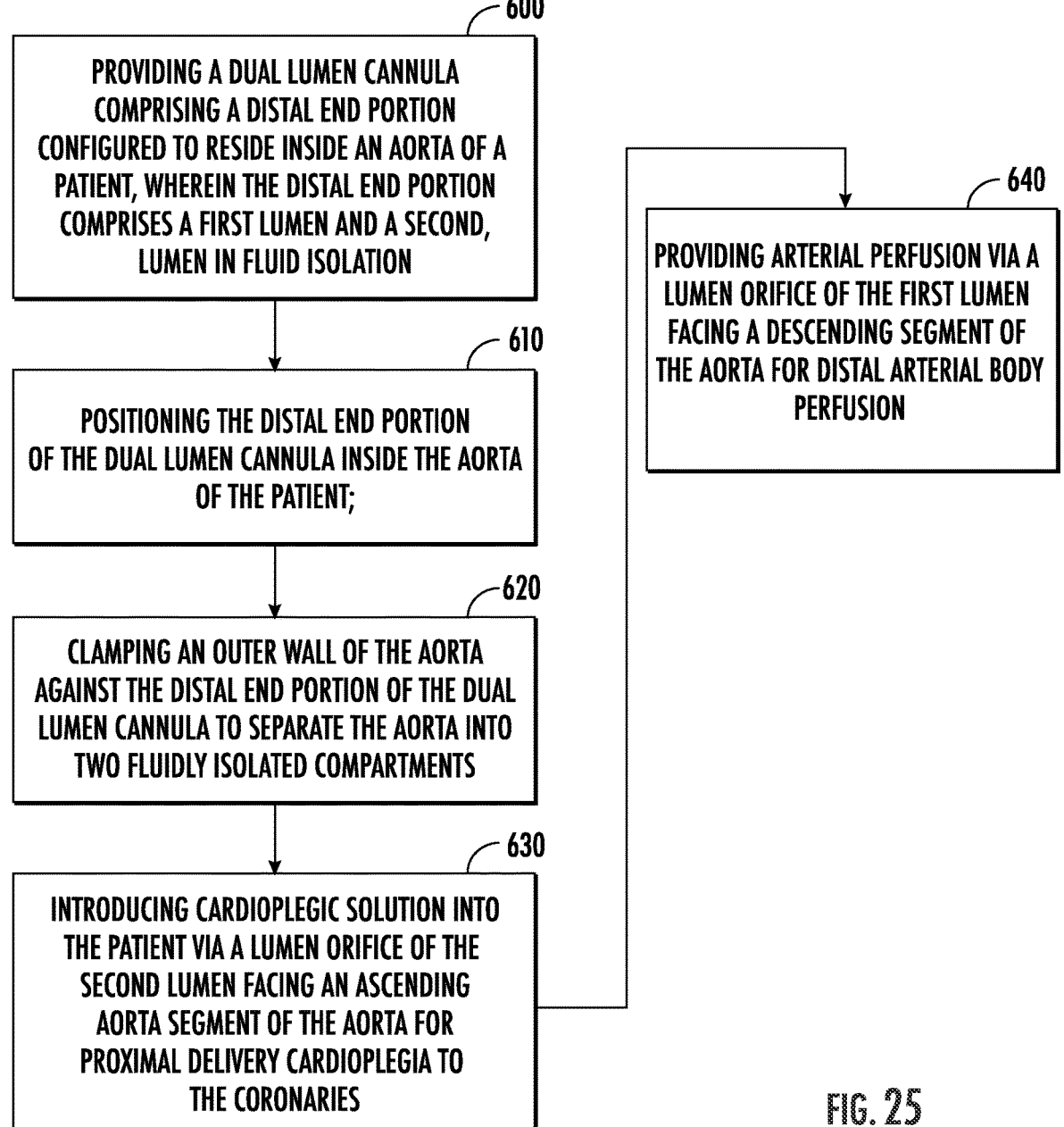

600

PROVIDING A DUAL LUMEN CANNULA COMPRISING A DISTAL END PORTION CONFIGURED TO RESIDE INSIDE AN AORTA OF A PATIENT, WHEREIN THE DISTAL END PORTION COMPRISES A FIRST LUMEN AND A SECOND, LUMEN IN FLUID ISOLATION

610

POSITIONING THE DISTAL END PORTION OF THE DUAL LUMEN CANNULA INSIDE THE AORTA OF THE PATIENT;

620

CLAMPING AN OUTER WALL OF THE AORTA AGAINST THE DISTAL END PORTION OF THE DUAL LUMEN CANNULA TO SEPARATE THE AORTA INTO TWO FLUIDLY ISOLATED COMPARTMENTS

630

INTRODUCING CARDIOPLEGIC SOLUTION INTO THE PATIENT VIA A LUMEN ORIFICE OF THE SECOND LUMEN FACING AN ASCENDING AORTA SEGMENT OF THE AORTA FOR PROXIMAL DELIVERY CARDIOPLEGIA TO THE CORONARIES

640

PROVIDING ARTERIAL PERFUSION VIA A LUMEN ORIFICE OF THE FIRST LUMEN FACING A DESCENDING SEGMENT OF THE AORTA FOR DISTAL ARTERIAL BODY PERFUSION

FIG. 25

DOUBLE LUMEN AORTIC CANNULA AND CROSS CLAMP ASSEMBLY AND RELATED METHODS

RELATED APPLICATIONS

This patent application claims the benefit of and priority to U.S. Provisional Application Ser. No. 63/069,799, filed Aug. 25, 2020, the contents of which are hereby incorporated by reference as if recited in full herein.

FIELD OF INVENTION

The present invention relates to medical devices for cardiac surgeries.

BACKGROUND

Many cardiac operations require cardiopulmonary bypass and myocardium protection. Cardiopulmonary bypass (CPB) is a technique that temporarily takes over the function of the heart and lungs during surgery, maintaining the circulation of blood and the oxygen content of the patient's body. The CPB pump itself is often referred to as a heart-lung machine. CPB is a form of extracorporeal circulation. CPB mechanically circulates and oxygenates blood for the body while bypassing the heart and lungs maintaining perfusion and creating bloodless surgical field for the surgeon. A CPB circuit consists of a systemic circuit for oxygenating blood and reinfusing blood into a patient's body (bypassing the heart).

In certain instances, cardioplegia is induced during cardiac operations. Cardioplegia is intentional and temporary cessation of cardiac activity and is used primarily for cardiac surgery. Myocardium protection, the prevention of ischemic heart muscle cell injury, can be accomplished with the administration of a cardioplegia solution. Cardioplegia prevents ischemia and cell injury of the heart muscle. A separate circuit is used to infuse cardioplegia solution into the heart muscle to produce cardioplegia and providing myocardial protection (i.e., to prevent the death of heart tissue).

Cardioplegia can be established by deliberate lowering of the temperature to reduce the metabolic rate, hypothermic cardioplegia. The main goals of hypothermic cardioplegia are: (1) immediate and sustained electromechanical quiescence, (2) rapid and sustained homogeneous myocardial cooling, (3) maintenance of therapeutic additives in effective concentrations, and (4) periodic washout of metabolic inhibitors.

In certain aspects, asystole, the arrest of cardiac rhythm, where no discernable electrical activity is detected by EKG, is induced. The most common procedure for accomplishing asystole is infusing cold cardioplegic solution into the coronary circulation. This process protects the myocardium, or heart muscle, from damage during the period of ischemia.

To achieve cardioplegia, the patient is first placed on cardiopulmonary bypass. The CPB device takes over the functions of gas exchange by the lung and blood circulation by the heart. Subsequently, the heart is isolated from the rest of the blood circulation by means of an occlusive cross-clamp placed on the ascending aorta proximal to the innominate artery. During this period of heart isolation, the heart is not receiving any blood flow, thus no oxygen for metabolism. Cardioplegia solution is infused immediately after, or simultaneously with, the placement of the cross clamp. The cardioplegia solution distributes to the entire myocardium, the EKG will change and eventually asystole will ensue.

Cardioplegia lowers the metabolic rate of the heart muscle, thereby preventing cell death during the ischemic period.

The aortic cross-clamp is a surgical instrument used in cardiac surgery to clamp the ascending aorta and separate the systemic circulation from the outflow of the heart where the entry or ostium of the coronary arteries are located. Many cardiac operations require placement in the ascending aorta of an arterial cannulation, an antegrade cardioplegia cannula and a cross clamp between the two cannulas. The cross clamp mechanically and functionally separates the ascending aorta in two compartments; (i) a compartment distal to the clamp perfused by the arterial cannula; and (ii) a compartment proximal to the clamp perfused by the cardioplegia cannula. The arterial cannula is used to return the oxygenated blood from the bypass machine to perfuse the rest of the body. The cardioplegia cannula is used to deliver cardioplegia solution in proximal ascending aorta, which is connected to the coronary arteries suppling the heart muscle.

FIG. 1 is an example prior art medical device system used in cardiac surgeries. The aorta A comprises coronary arteries 1, an ascending aorta 2, a distal ascending and aortic arch 3 and a descending aorta 4. The arterial cannula 5 is inserted in the aortic arch and/or distal ascending aorta 3 to provide arterial perfusion. The cardioplegia cannula 6 is placed in the proximal ascending aorta 2 to perfuse the coronary arteries 1 with (tepid) cardioplegia solution. The cross clamp 7 is placed between the respective cannulas arterial and cardioplegia, 5, 6, respectively. The clamp 7 provides mechanical separation between aortic segments. The separation allows continuous arterial perfusion and intermittent delivery of the cardioplegia.

Atheromatous disease is a medical condition in which lipid rich material accumulate in the wall of the vessels forming plaques. The rupture of the plaque surface inside the vessel can cause thrombosis, emboli, ischemia and infarction. These adverse events are known as heart attacks, myocardium infarction, mesenteric ischemia, limb ischemia and neurological stroke. A certain degree of aortic manipulation is necessary to perform aortic cannulation and to place the cross clamp, which can increase the risk of adverse events. Overall, it is believed that cardiac surgery is associated with about a 3-5% risk of neurological strokes and emboli from aortic manipulation is considered the main source of emboli.

The disruption of atheromatous plaques and emboli can also occur secondary to the positioning of the cannula against the aortic wall. The blood to perfuse the entire body is delivered under elevated pressure, the exit of the blood at the tip of the cannula has elevated blood flow velocity and can cause "sand blasting effect" in intimal layer of the aorta.

An important factor in cardiac operations is the time to perform the operation. The institution of cardiopulmonary bypass is just the initial step of the operation. Several other tasks are necessary to repair cardiac defect. As discussed above, conventional systems require the placement of two separate cannulas via separate incisions and a cross clamp between the cannulas. For every cannula inserted in the heart, it is necessary to stitch the vessel wall to create a seal and to prevent the cannulas from moving.

There is a need for alternative medical devices to improve safety, efficiency and/or effectiveness of arterial cannulation and cross clamping.

SUMMARY

Embodiments of the present invention provide a solution to the problems associated with cannulation and cross clamp procedures described hereinabove.

Embodiments of the invention provide a surgical device for cardiac surgery that may reduce the incidence of stroke associated therewith by reducing manipulation and mechanical stress on/in the aortic wall.

In certain embodiments, a cardiothoracic medical device includes a double lumen cannula and a clamp assembly. The double lumen cannula and clamp assembly can be separate components with at least one aligning and interlocking feature. Therefore, the cannula can be inserted, cardiopulmonary bypass can be initiated, and the clamp assembly can be placed afterwards. The medical device allows mechanical isolation of the aorta about the cannula, and arterial perfusion and delivery of cardioplegia in opposite directions.

In certain embodiments, the lumens differ in size with one larger than the other. The larger lumen is for arterial perfusion. The smaller lumen is for antegrade cardioplegia.

The double lumen cannula is configured to be inserted into the aorta after a small opening of the aorta wall or using a needle and over a wire technique.

Each lumen has a respective orifice. The orifices open and face in opposite directions. One orifice for the arterial perfusion opens towards the distal ascending aorta and the other orifice for cardioplegia opens towards the aortic root.

The cannula and clamp are separate components that are coupled after the arterial cannulation. The cannula and clamp can be assembled during use, forming a perfusion assembly.

In certain embodiments, the cannula and clamp are configured to interlock or couple forming the assembly.

In certain embodiments, the cannula provides an alignment component that is received by the clamp.

In certain embodiments, the clamp provides an alignment component that is received by the cannula.

In certain embodiments, the clamp and cannula provide alignment components that interact or interlock to form a cannula/clamp assembly during use.

The cannula or clamp can have an aligner pin that couples with the clamp or cannula, respectively. The aligner pin can extend through an aperture in a center of the cross-clamp hinge.

The aligner stabilizes, positions and couples the clamp and the cannula without interfering with the clamp mechanism.

The coupling pin can have a separate locking segment or member for the clamp to adjust with the desired position of the cannula.

The internal surface of clamp arms can be configured to mirror the external surface and shape of the cannula that is inserted inside the vessel. After final positioning of cannula and clamp, the orifices for both lumens point in opposite directions. The larger orifice for arterial perfusion will point to the distal aorta and small orifice for anterior cardioplegia will point to the proximal aorta.

Aspects of the invention are directed to cardiothoracic surgical devices that include a dual lumen cannula with a distal end portion configured to reside inside an aorta of a patient. The distal end portion has a first lumen and a second lumen in fluid isolation. The first lumen has a lumen orifice that faces a first direction inside the aorta and the second lumen comprises a lumen orifice that faces a second direction that is different than the first direction inside the aorta. The devices also include: a first conduit that is coupled to the first lumen and that extends outside the aorta and has a length sufficient to extend externally from a patient; a second conduit that is coupled to the second lumen and that extends outside the aorta with a length sufficient to extend externally from the patient; and a clamp assembly coupled to the dual lumen cannula and configured with first and second clamp arms that are configured to align with the distal end portion of the dual lumen cannula and clamp against opposing external surfaces of a vessel wall of the aorta to thereby compress the vessel wall against the distal end portion of the dual lumen cannula and thereby provide first and second fluidly isolated segments of the aorta.

The dual lumen cannula can further include a coupling pin that is configured to extend outside the aorta and that couples to the clamp assembly.

The distal end portion can have a tapered closed tip that is configured to face and abut an inner surface of the vessel wall of the aorta.

The distal end portion can be defined by a unitary body.

The unitary body can have increased rigidity relative to the first and second conduits.

The first conduit can have a greater inner diameter than the second conduit.

The second conduit can merge into a connector interface that couples first and second tubes to the second conduit thereby allowing separate fluid channels for venting and introducing cardioplegia solution, respectively.

The distal end portion can have a connector interface with first and second branches that resides outside and adjacent the vessel wall of the aorta.

The distal end portion can have an internal solid wall that separates the first lumen and the second lumen. The first orifice can have a longer longitudinal extent than the second orifice.

The distal end portion can have a hub that is external to the aorta and merges into a segment with a tip that resides entirely in the aorta.

The unitary body can have a top with a connection interface that can define first and second branches that couple to the first and second conduits, respectively.

The clamp assembly can have an aperture that slidably receives the coupling pin, optionally the aperture is provided in a hinge segment of the clamp assembly.

The clamp assembly can have a deployment assembly coupled to an elongate shaft, and wherein the elongate shaft is coupled to an actuator that directs the deployment assembly to close the clamp arms against the distal end portion of the dual lumen cannula.

The device may include a lock member that is configured to lock the clamp assembly to the dual lumen cannula.

The clamp assembly can have a first arcuate leg that is connected to the first clamp arm and a second arcuate leg that is connected to the second clamp arm. In a closed position, the first and second clamp arms can be aligned with the distal end portion of the dual cannula.

The device can also include an ultrasound probe coupled to the clamp assembly and/or coupled to the dual lumen cannula.

The first and second clamp arms can have a material on an inner facing segment that clamps against the aorta that has less rigidity than another material of the first and second clamp arms.

Still other aspects are directed to methods of providing a cardiac treatment. The methods include providing a dual lumen cannula with a distal end portion configured to reside inside an aorta of a patient. The distal end portion has a first lumen and a second lumen in fluid isolation. The method further includes: positioning the distal end portion of the dual lumen cannula inside the aorta of the patient; clamping an outer wall of the aorta against the distal end portion of the dual lumen cannula to separate the aorta into two fluidly isolated compartments; introducing cardioplegic solution into the patient via a lumen orifice of the second lumen facing an ascending aorta segment of the aorta for proximal delivery of cardioplegia to the coronaries; and providing arterial perfusion via a lumen orifice of the first lumen facing a descending segment of the aorta for distal arterial body perfusion.

The clamping can be carried out using a clamp assembly with first and second clamp legs connected to first and second clamp arms, respectively. The method can further include locking the clamp assembly to the dual lumen cannula before clamping the first and second clamp arms against the outer wall of the aorta and the distal end portion of the dual lumen cannula.

The clamping can be carried out using an elongate shaft coupled to an actuator and a clamp assembly providing the clamping step.

The method can also include using an ultrasound probe located on a clamp assembly or the dual lumen cannula to visualize placement of the dual lumen cannula at a desired location in the aorta and/or to visualize closure of clamp arms against the aorta and distal end portion of the dual lumen cannula.

The clamping can be carried out using a clamp assembly with first and second clamp legs connected to first and second clamp arms, respectively. The dual lumen cannula can be positioned inside the aorta using a single incision whereby the dual lumen cannula and clamp assembly reduces manipulation and mechanical stress in the aortic wall over a corresponding cardiac surgery carried out using two separate cannulas and a cross-clamp.

Further features, advantages and details of the present invention will be appreciated by those of ordinary skill in the art from a reading of the figures and the detailed description of the preferred embodiments that follow, such description being merely illustrative of the present invention.

It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim or file any new claim accordingly, including the right to be able to amend any originally filed claim to depend from and/or incorporate any feature of any other claim although not originally claimed in that manner. These and other objects and/or aspects of the present invention are explained in detail in the specification set forth below.

BRIEF DESCRIPTION OF THE DRAWINGS

FIGS. 22A and 22B show the clamp in an unclamped orientation and the lock in an unlocked state. FIG. 22E shows the clamp closed and the lock unlocked. FIG. 22F shows the clamp closed and locked according to embodiments of the present invention.

FIG. 25 is a block diagram of example actions that can be performed during a cardiac surgery according to embodiments of the present invention.

Figure 1:
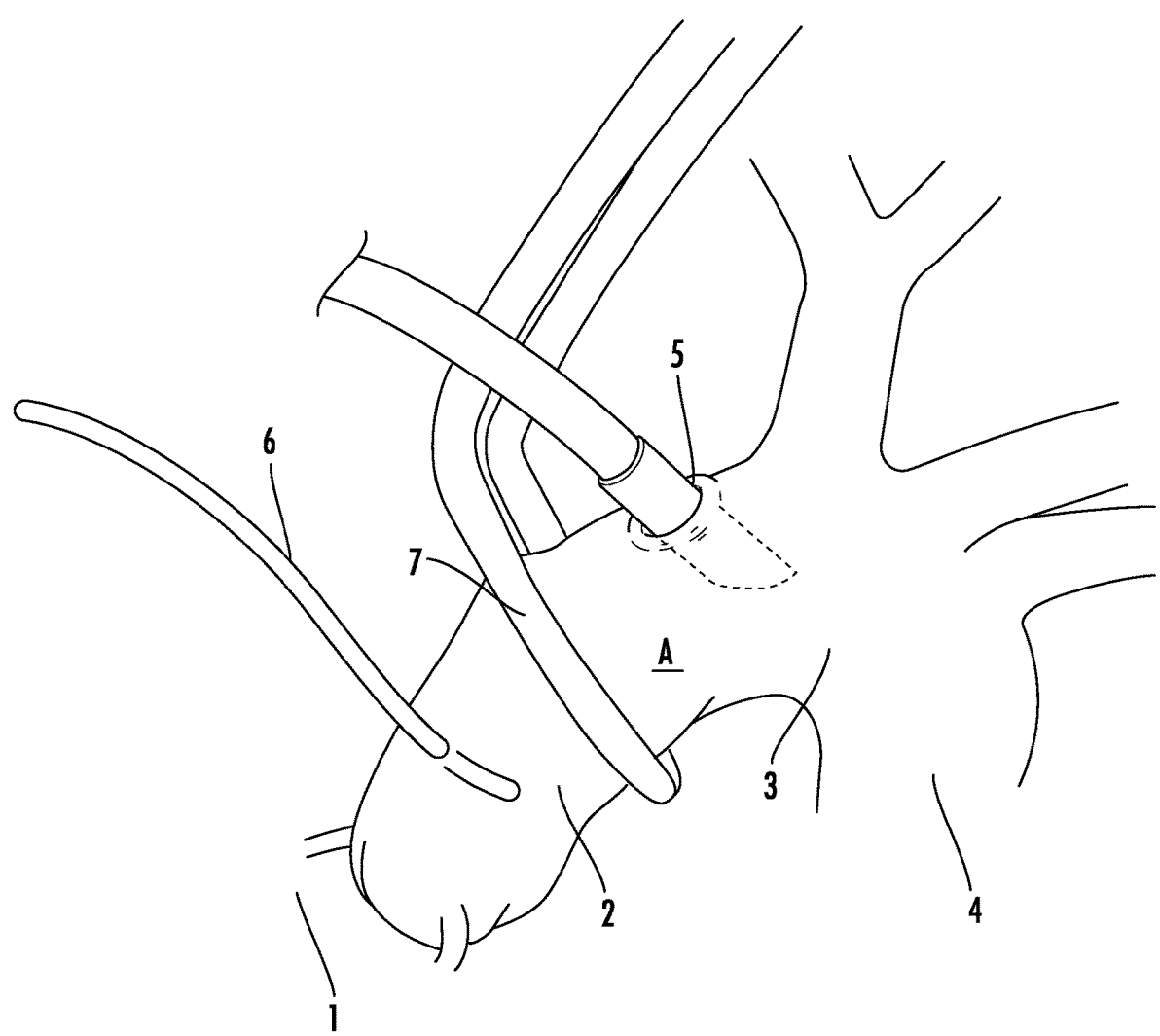
FIG. 1 is a schematic illustration of a prior art system used in cardiac surgeries.
Figure 2:
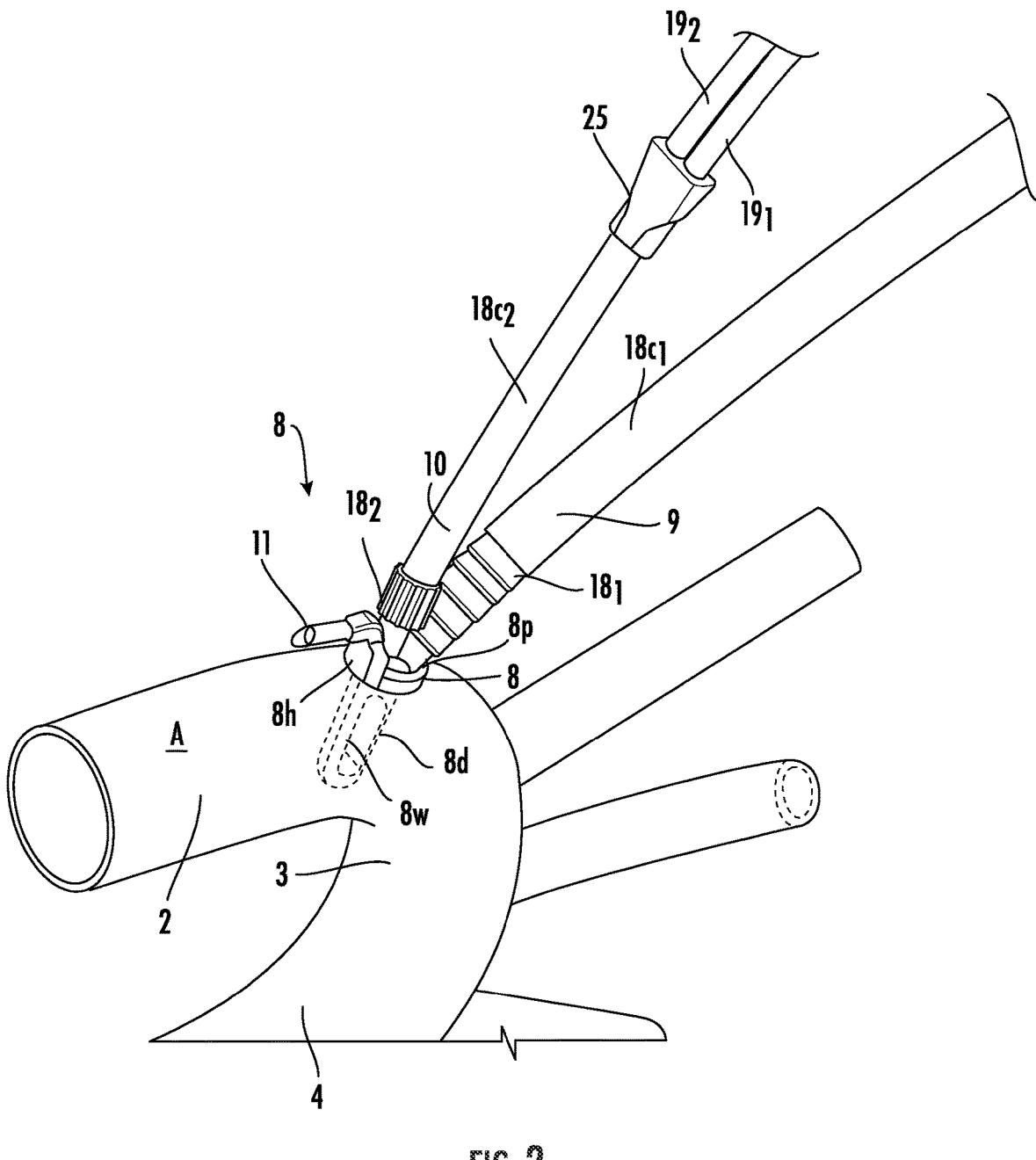
FIG. 2 is a perspective view of an example double lumen cannula according to embodiments of the present invention, shown placed in the ascending aorta.
Figure 3:
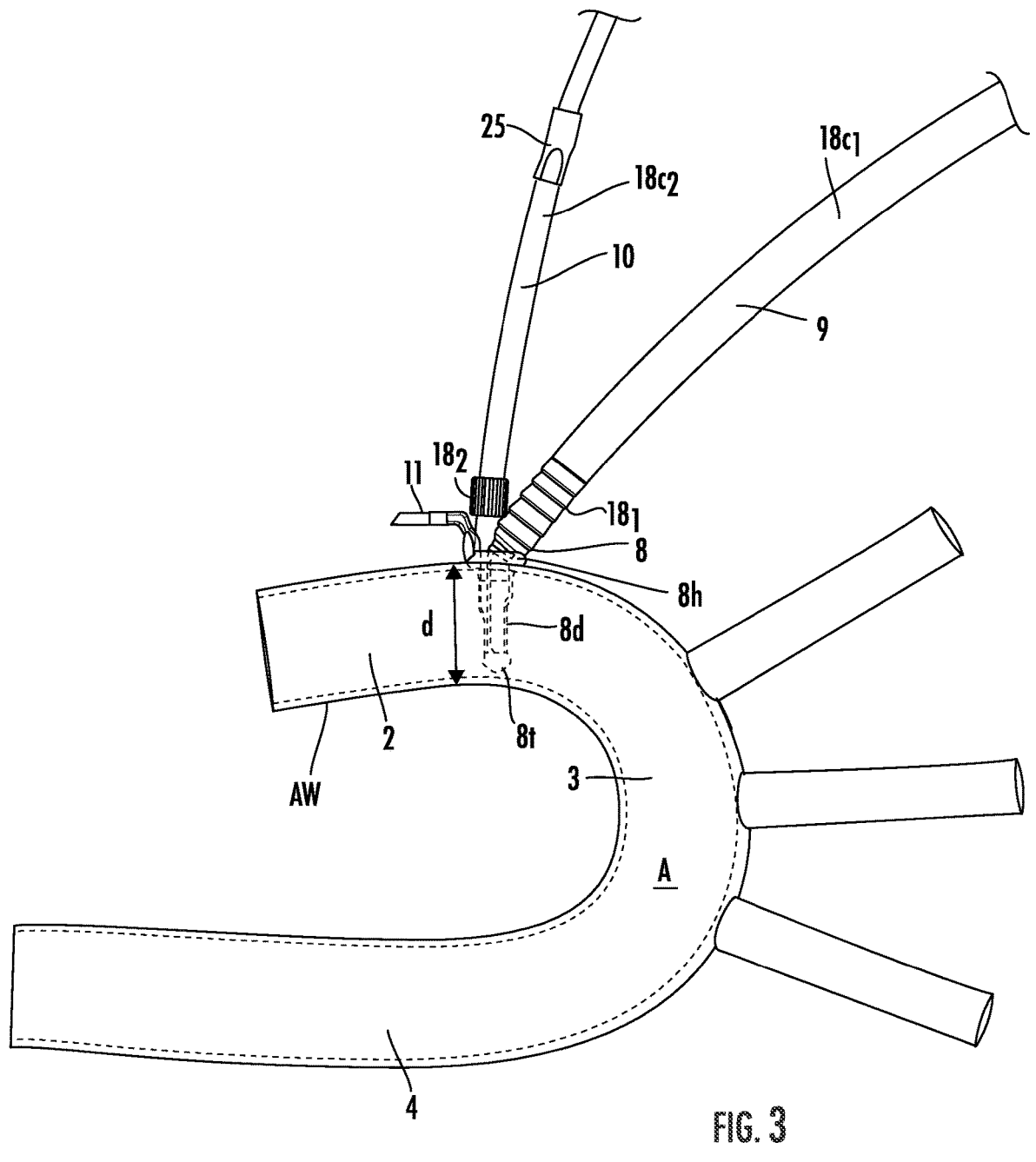
FIG. 3 is a lateral view of the double lumen cannula shown in FIG. 2.

Further features, advantages and details of the present invention will be appreciated by those of ordinary skill in the art from a reading of the figures and the detailed description of the preferred embodiments that follow, such description being merely illustrative of the present invention.

DETAILED DESCRIPTION

The present invention now will be described more fully hereinafter with reference to the accompanying drawings, in which illustrative embodiments of the invention are shown. Like numbers refer to like elements and different embodiments of like elements can be designated using a different number of superscript indicator apostrophes (e.g., 10, 10', 10", 10'").

In the drawings, the relative sizes of regions or features may be exaggerated for clarity. This invention may, however, be embodied in many different forms and should not be construed as limited to the embodiments set forth herein; rather, these embodiments are provided so that this disclosure will be thorough and complete, and will fully convey the scope of the invention to those skilled in the art.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath", "below", "lower", "above", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90° or at other orientations) and the spatially relative descriptors used herein interpreted accordingly. The term "about" refers to numbers in a range of +/−20% of the noted value. Any numerical range stated to be between two numbers is inclusive of the end point numbers.

As used herein, the singular forms "a", "an" and "the" are intended to include the plural forms as well, unless expressly stated otherwise. It will be further understood that the terms "includes," "comprises," "including" and/or "comprising," when used in this specification, specify the presence of stated features, integers, steps, operations, elements, and/or components, but do not preclude the presence or addition of one or more other features, integers, steps, operations, elements, components, and/or groups thereof. It will be understood that when an element is referred to as being "connected" or "coupled" to another element, it can be directly connected or coupled to the other element or intervening elements may be present. As used herein, the term "and/or" includes any and all combinations of one or more of the associated listed items.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and will not be interpreted in an idealized or overly formal sense unless expressly so defined herein.

Turning now to FIGS. 2-5, an example double cannula 8 with first and second lumens 9, 10, respectively is shown. The term "dual" is used interchangeably with the term "double" with respect to the cannula 8 herein. The first lumen 9 can be configured for arterial perfusion. The second lumen 10 can be configured for delivery of cardioplegia. The first and second lumens 9, 10 are in fluid isolation from each other. The first lumen 9 merges into a first lumen orifice 13. The second lumen 10 merges into a second lumen orifice 15. The first and second lumen orifices 13, 15 face different directions. The first lumen 9 can have larger diameter than the second lumen 10, typically at least twice the outer diameter or cross-sectional width than the second lumen 10. In some particular embodiments, the first lumen can be about 20 F. The second lumen 10 can have smaller diameter than the first lumen 9, optionally about 2 mm, in some particular embodiments.

Figure 14:
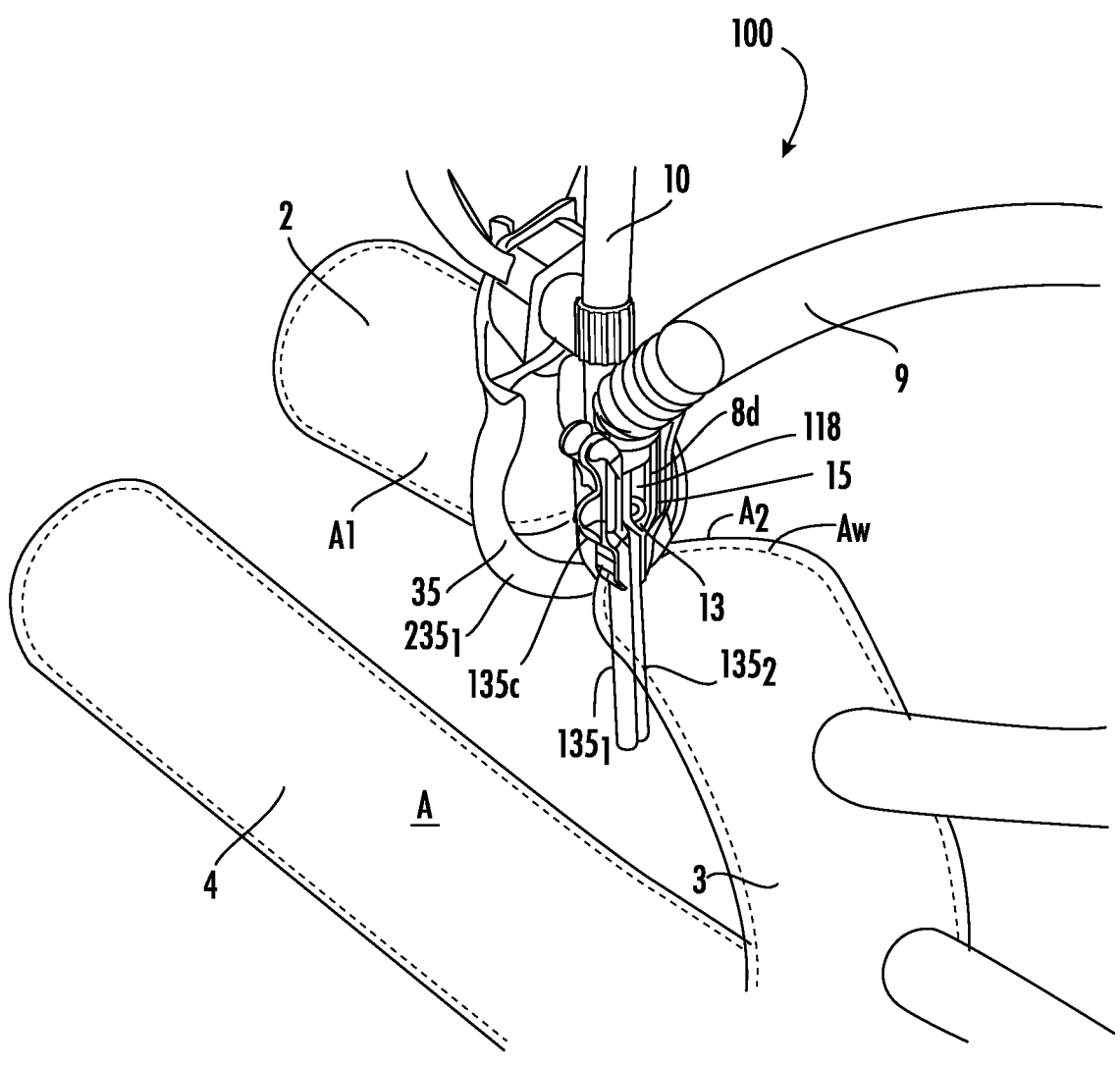
FIG. 14 is a side perspective, partially transparent view of the clamp and double lumen cannula with the clamp in a closed position against the double lumen cannula inside the aorta according to embodiments of the present invention.
Figure 15:
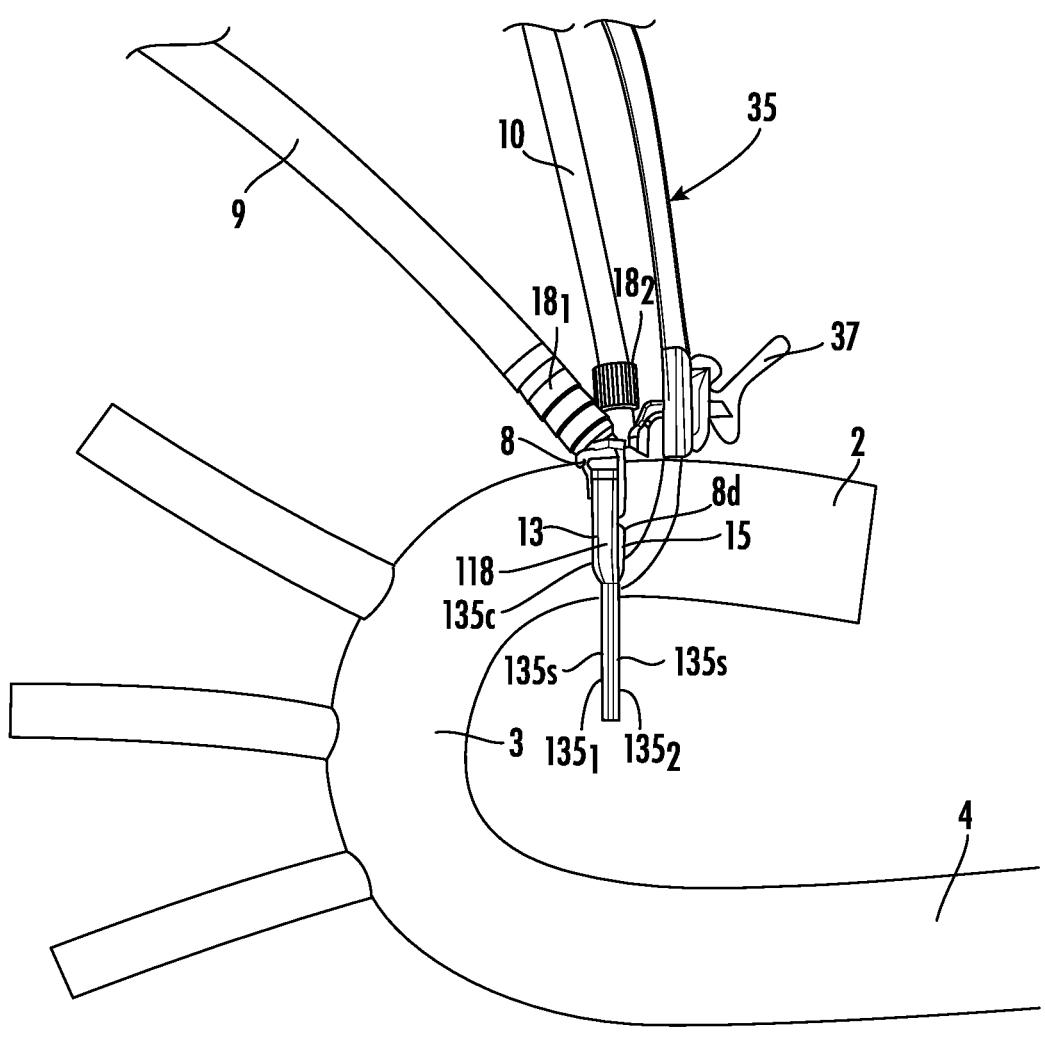
FIG. 15 is a side view of the clamp and double lumen cannula with the aorta shown in section view and with the clamp in the closed position shown in FIG. 14.
Figure 16:
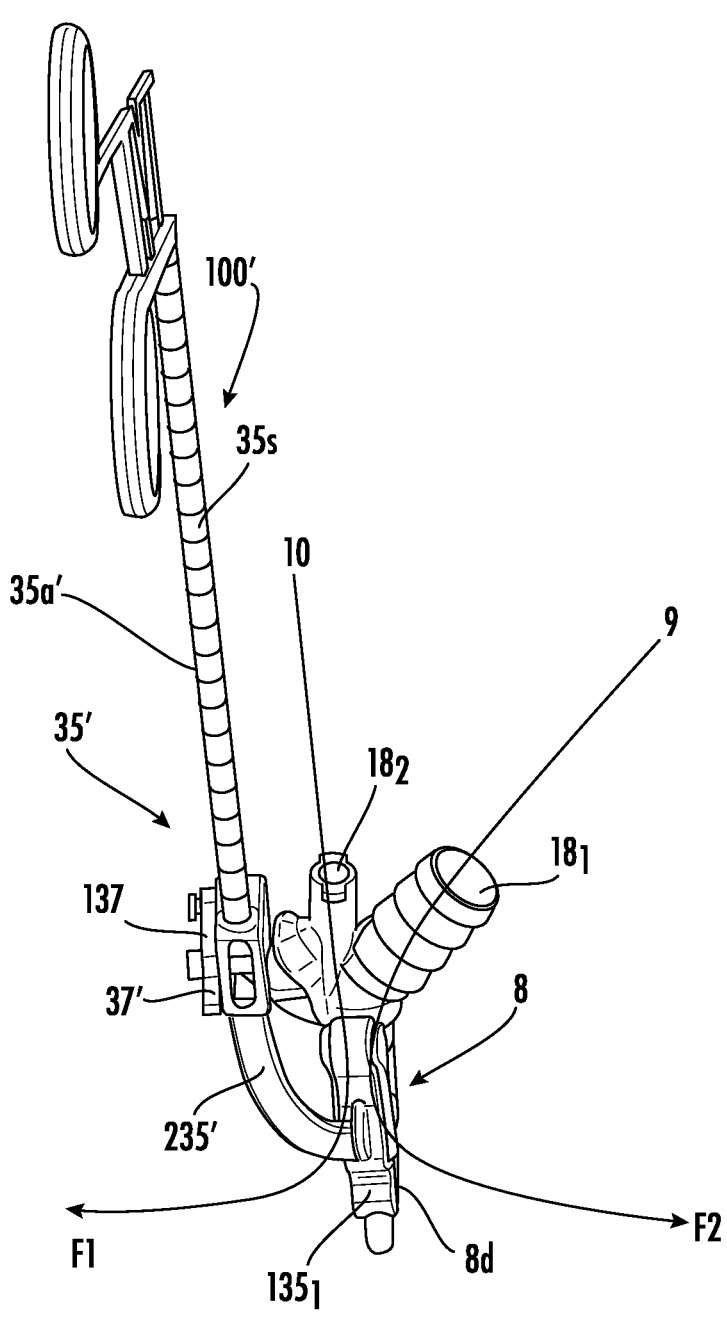
FIG. 16 is a top, side perspective view of another embodiment of a clamp and double lumen cannula assembly according to embodiments of the present invention.
Figure 17:
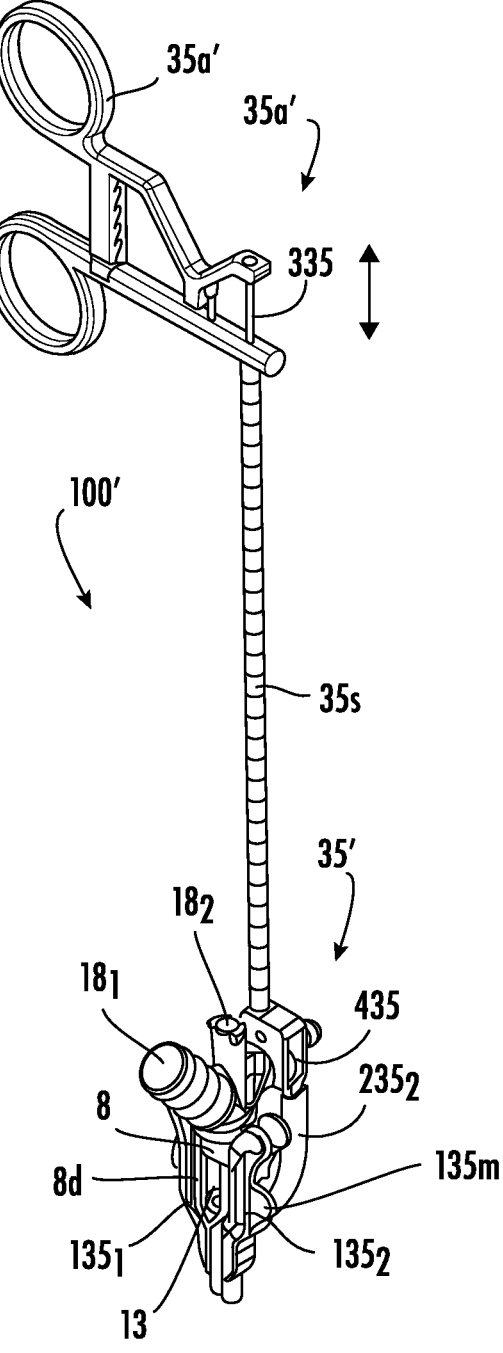
FIG. 17 is a side perspective view of the clamp and double lumen canula assembly shown in FIG. 16.
Figure 18A:
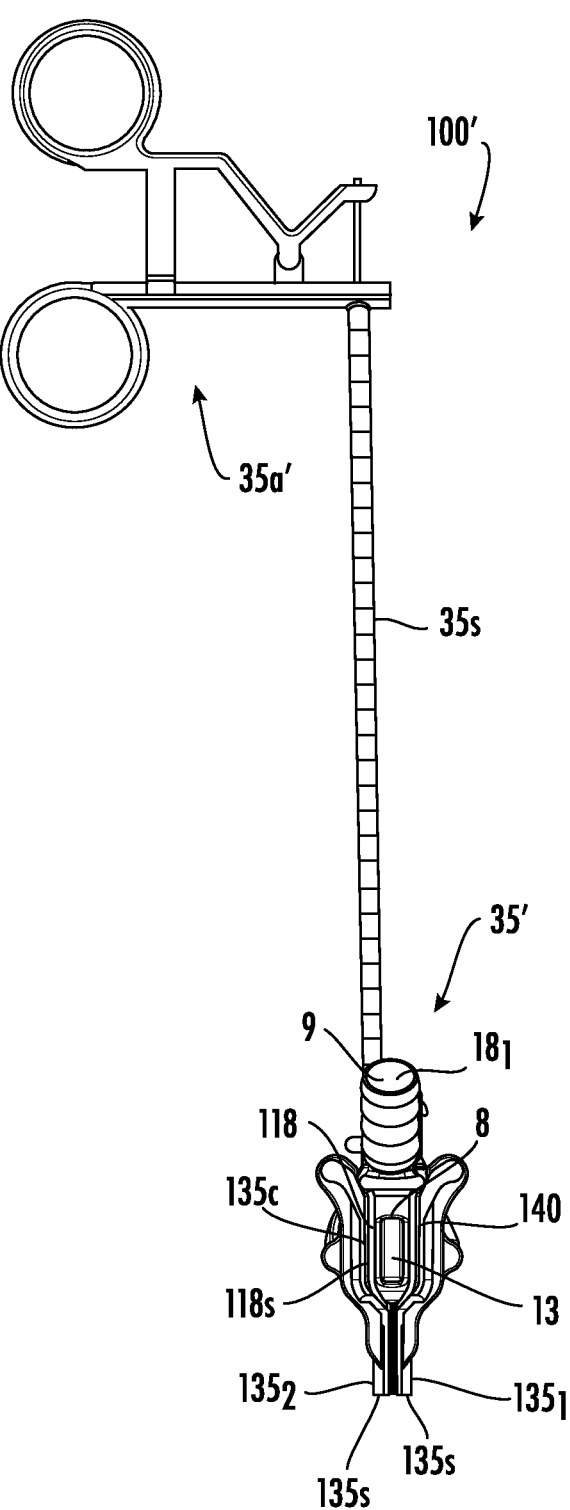
FIGS. 18A-18D are different side views of the clamp and double lumen cannula assembly shown in FIG. 17.
Figure 18B:
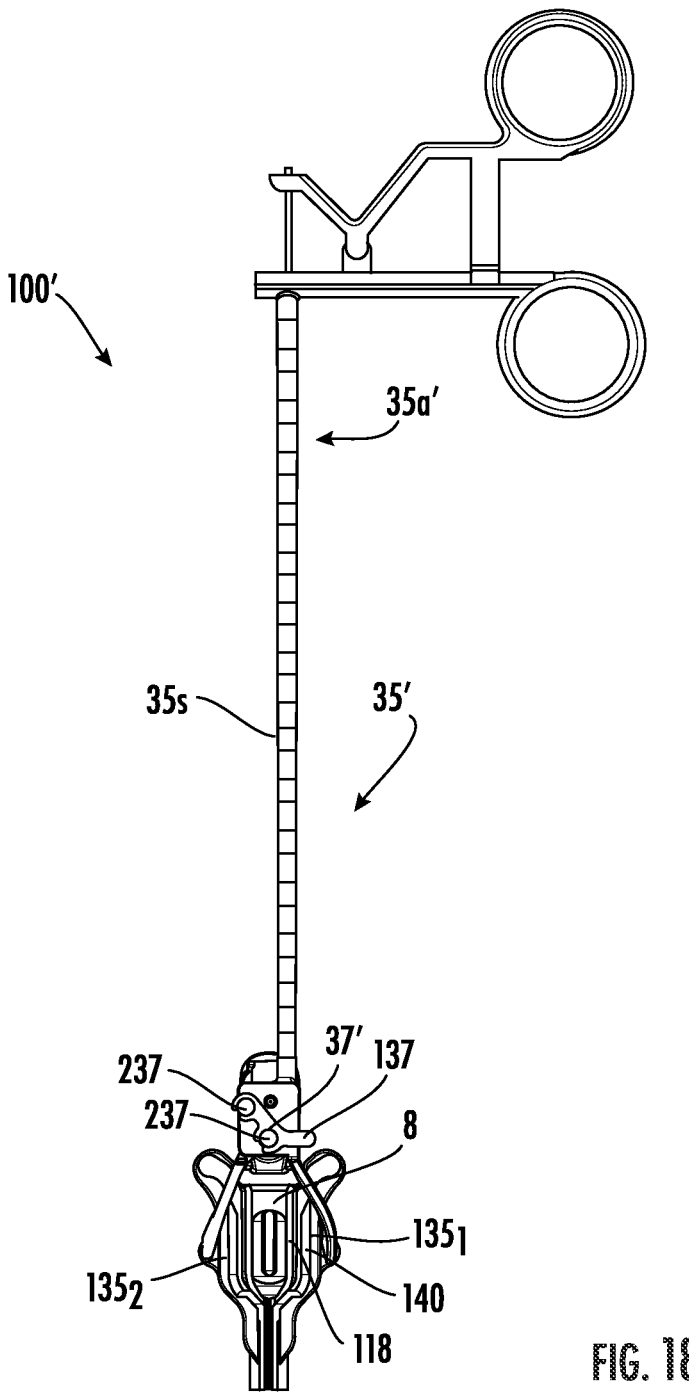
Figure 18C:
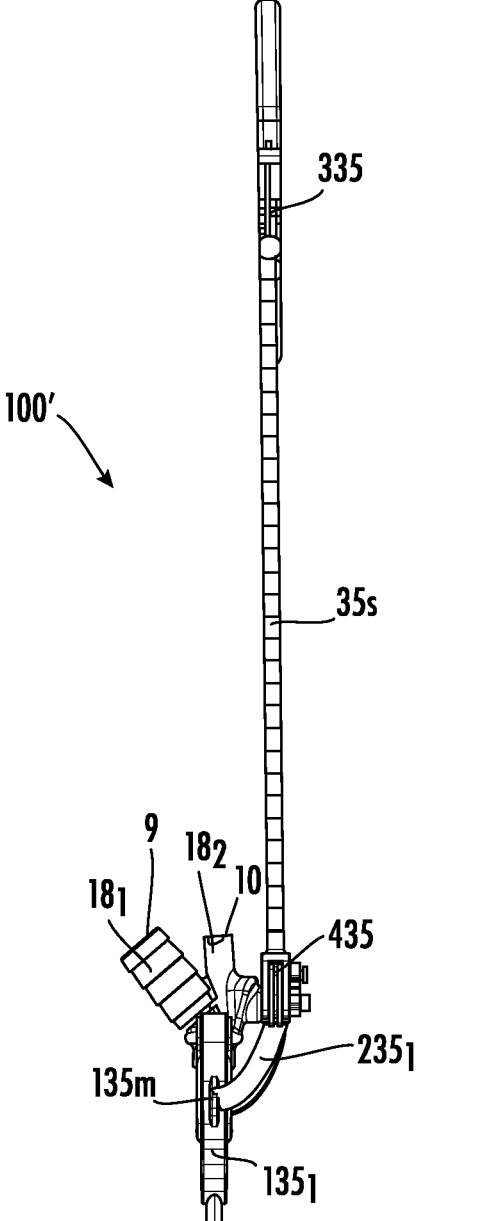
Figure 18D:
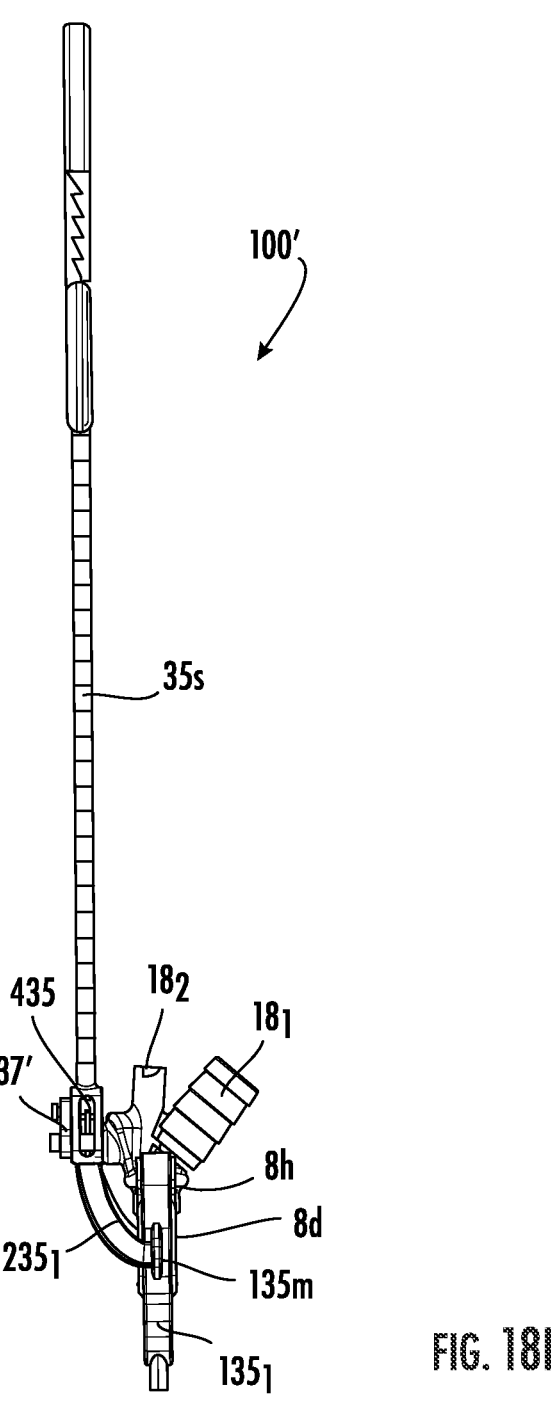
Figures 19A, 19B:
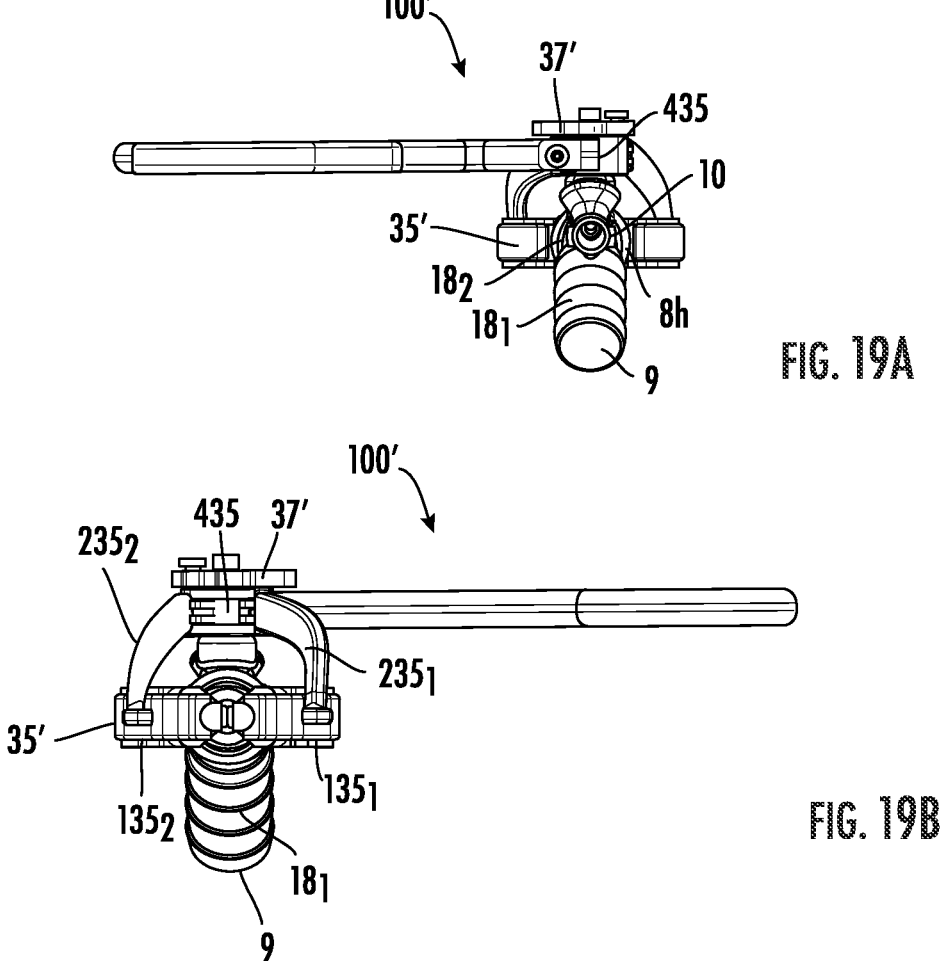
FIGS. 19A and 19B are different top views of the clamp and double lumen claim assembly shown in FIG. 16.
Figure 20A:
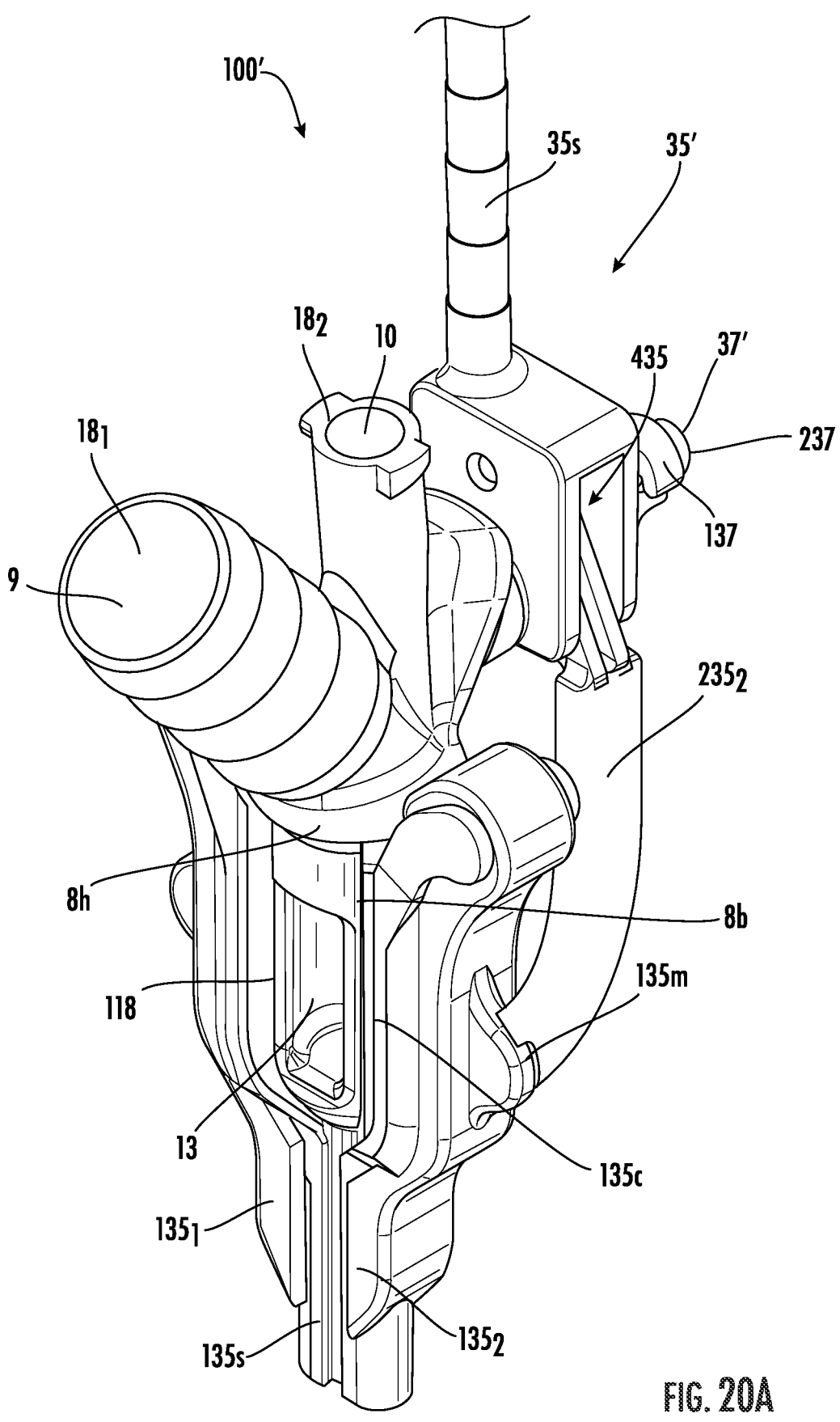
FIGS. 20A-20E, 21A and 21B are greatly enlarged views of a portion of the clamp and double lumen assembly shown in FIG. 16.
Figure 20B:
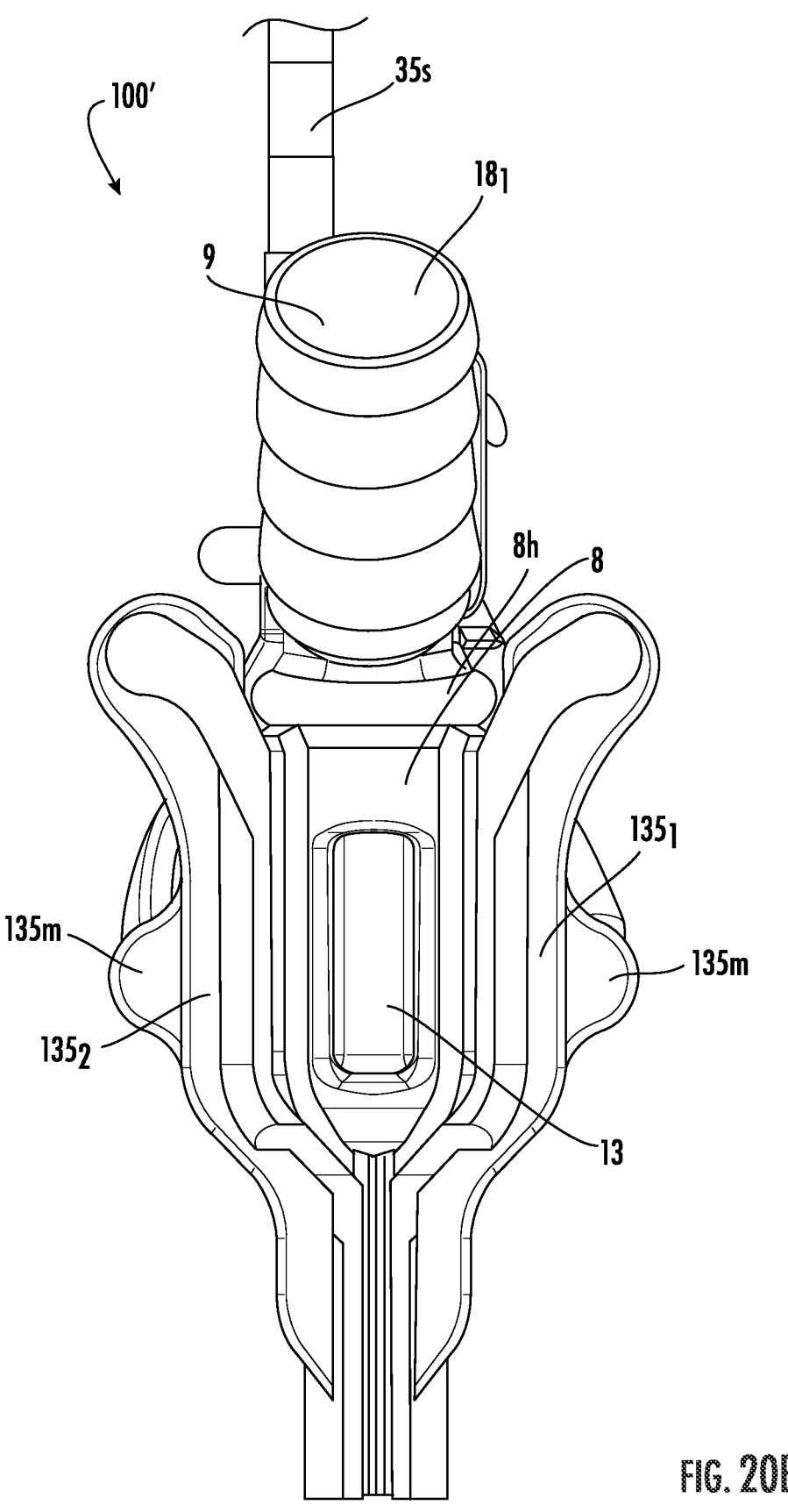
Figure 20C:
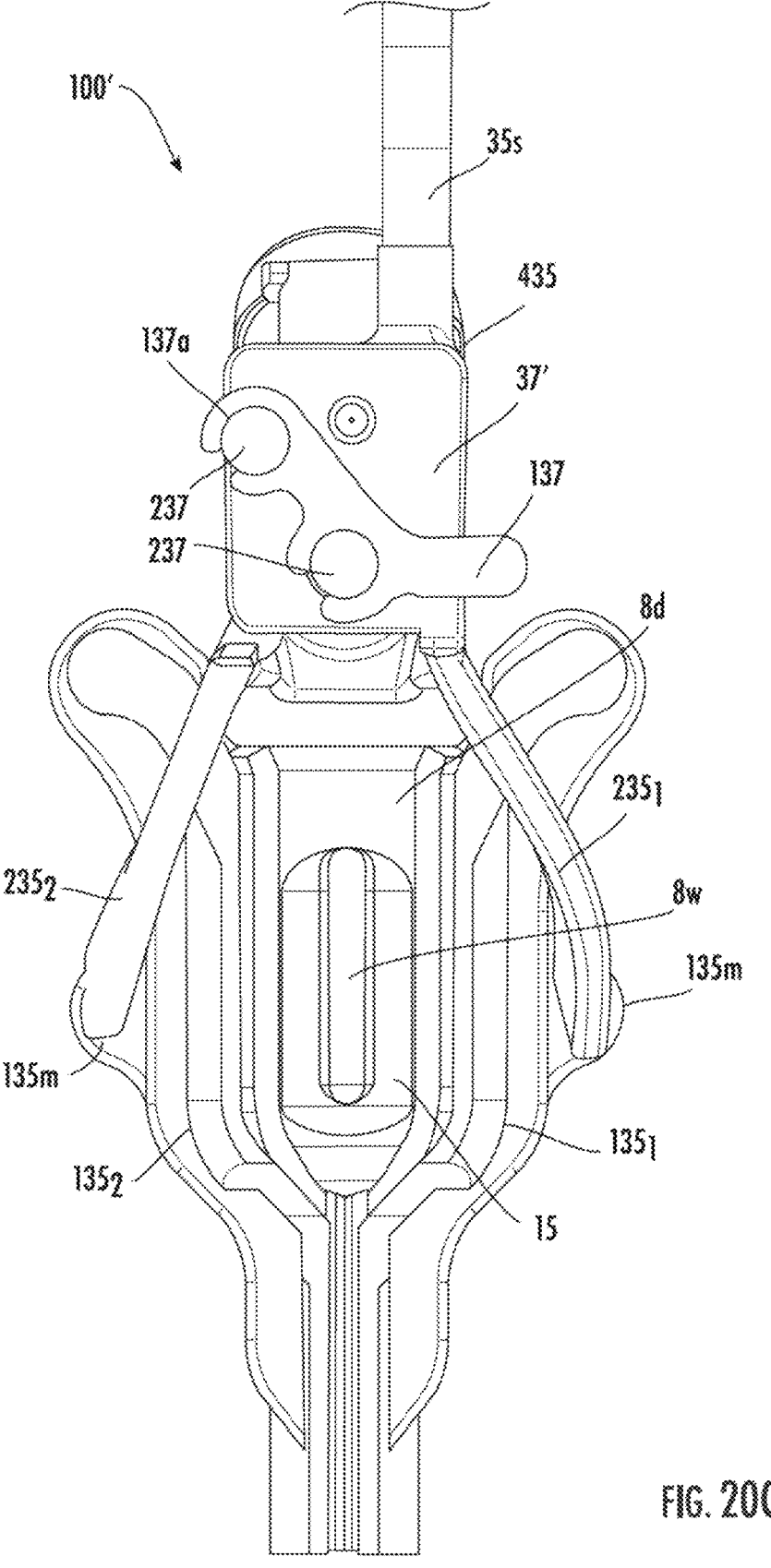
Figure 20D:
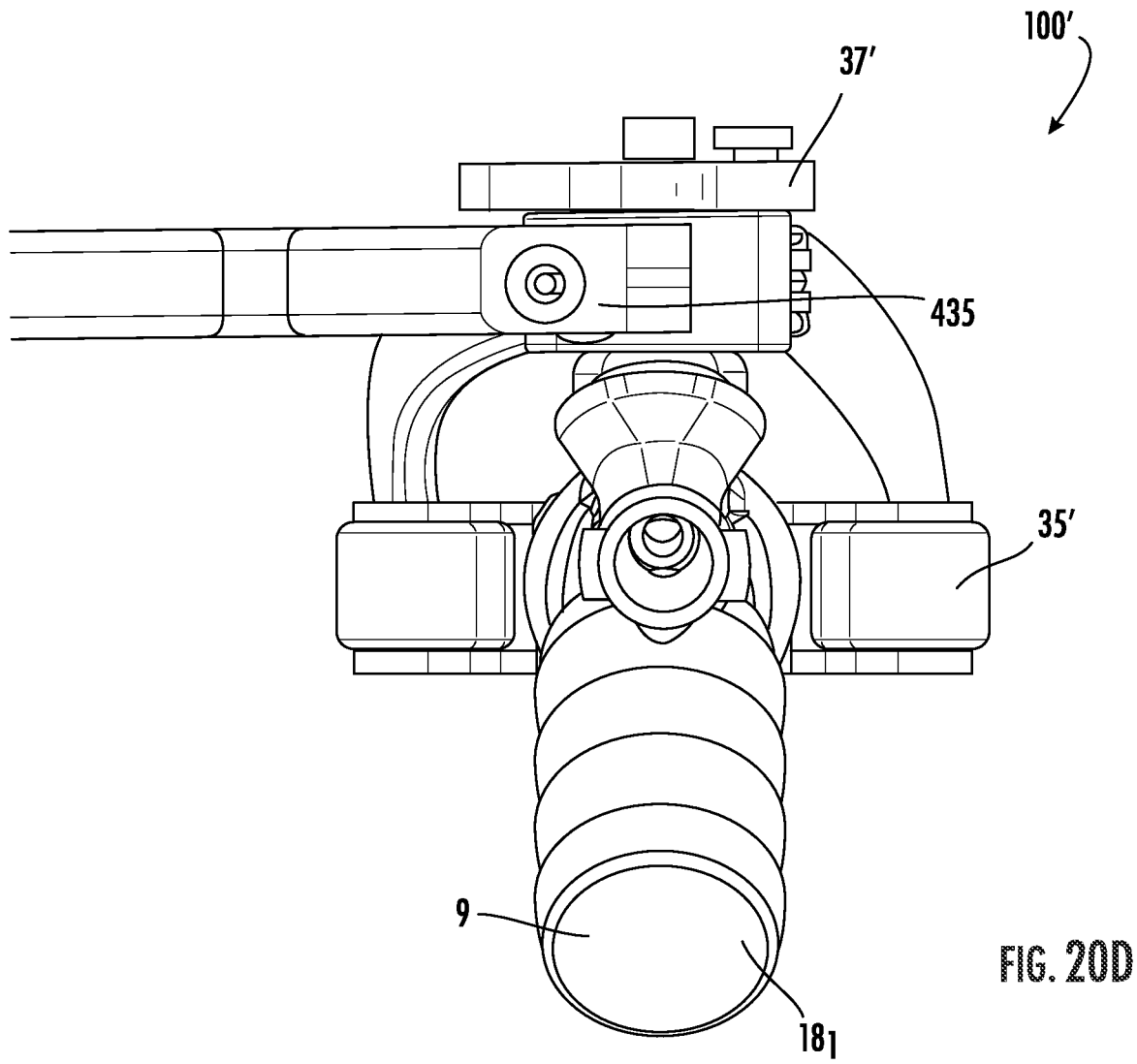
Figure 20E:
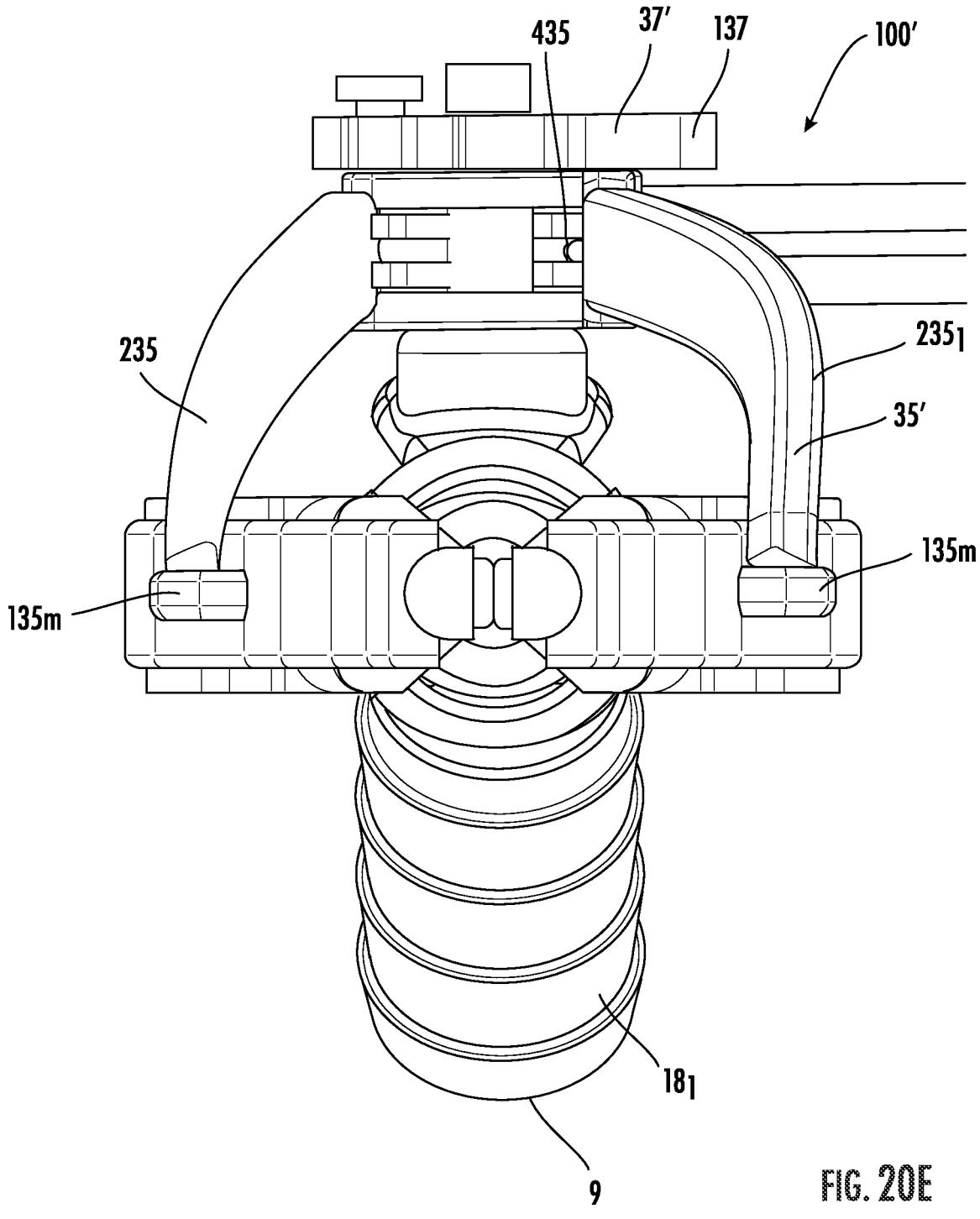
Figure 21A:
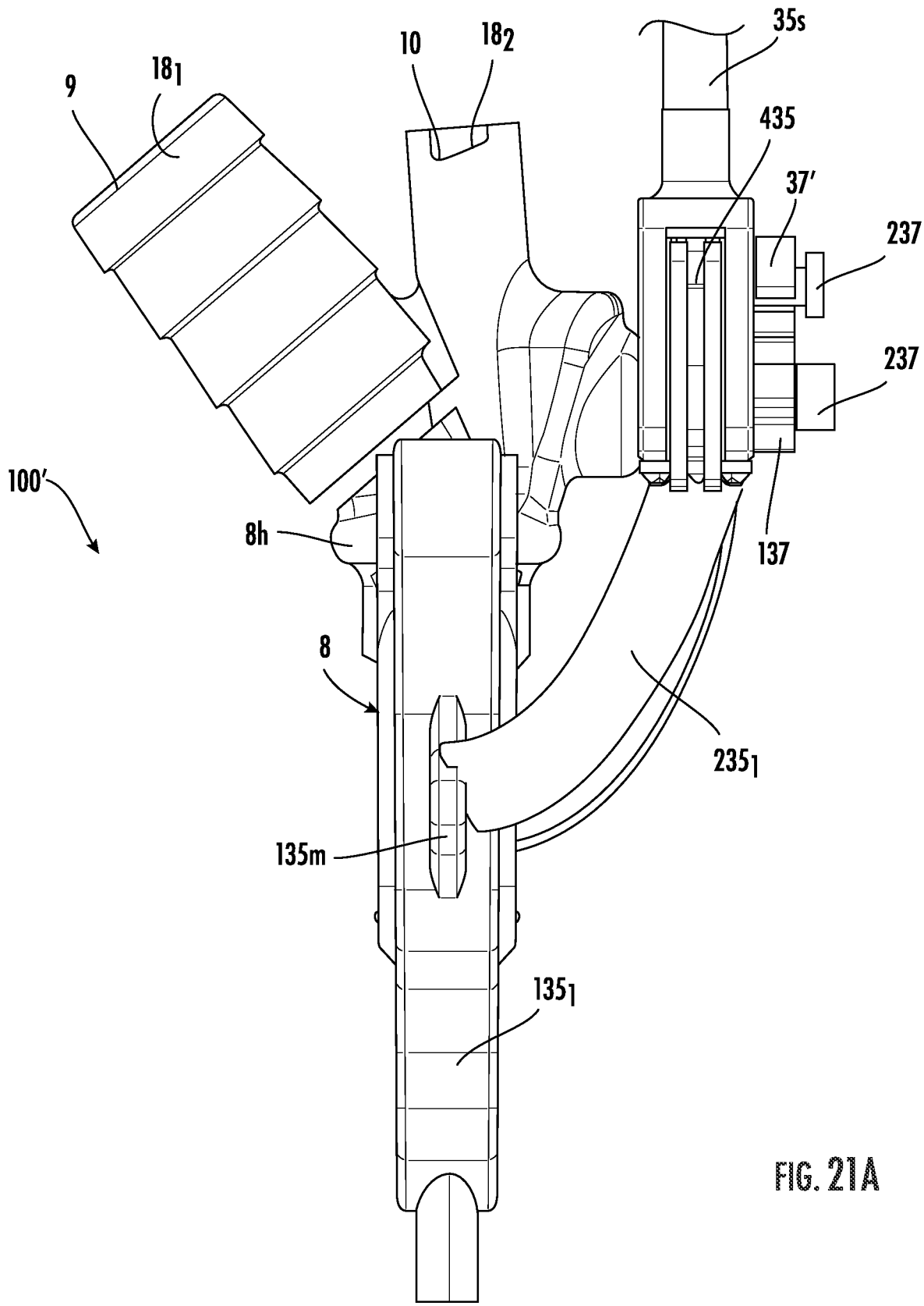
Figure 21B:
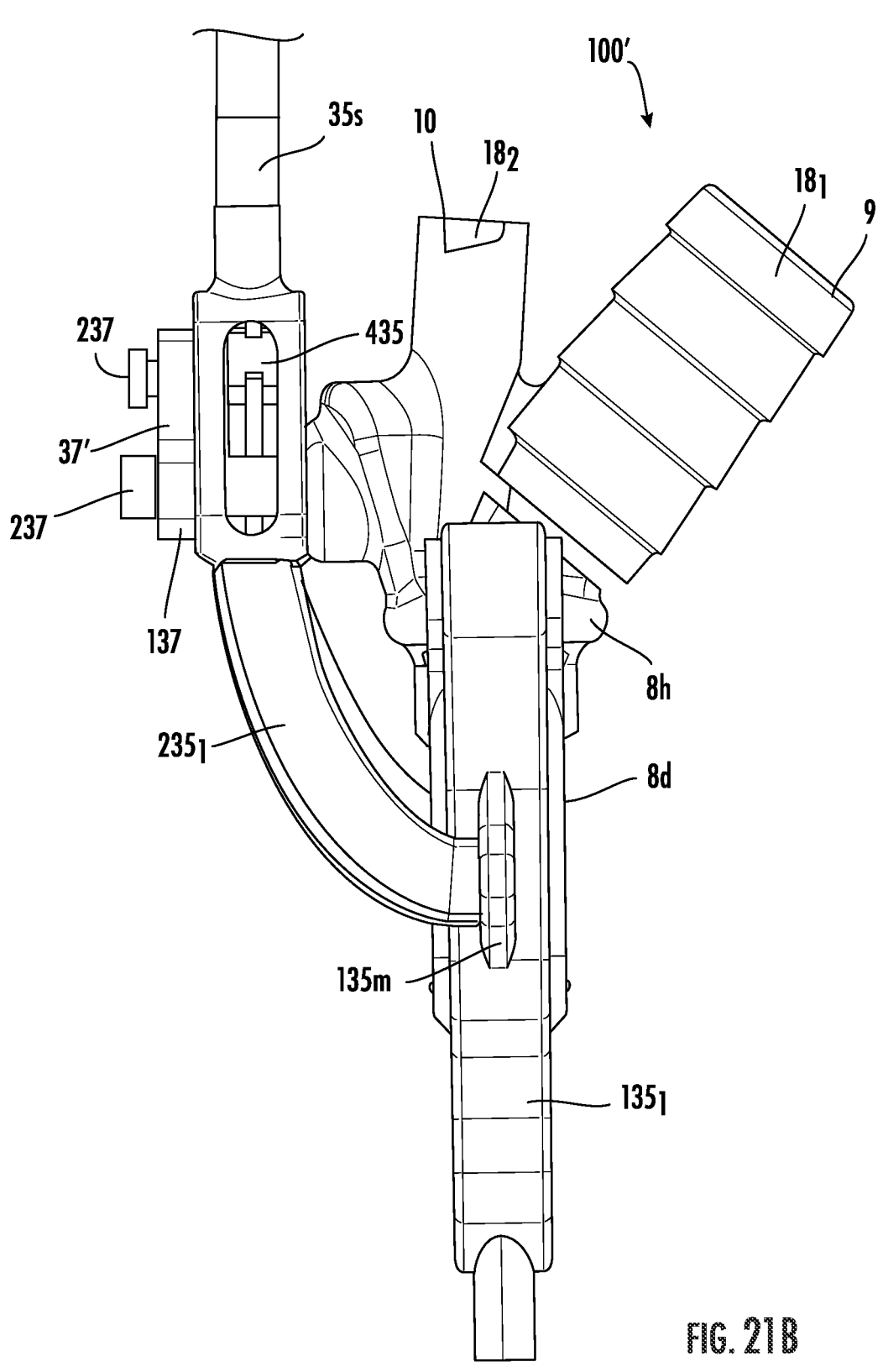
Figure 22A:
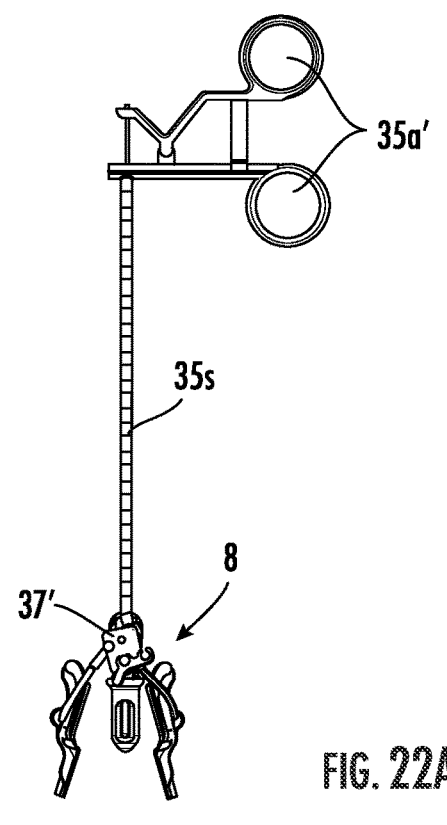
FIGS. 22A-22F are additional views of the assembly shown in FIG. 16.
Figure 22B:
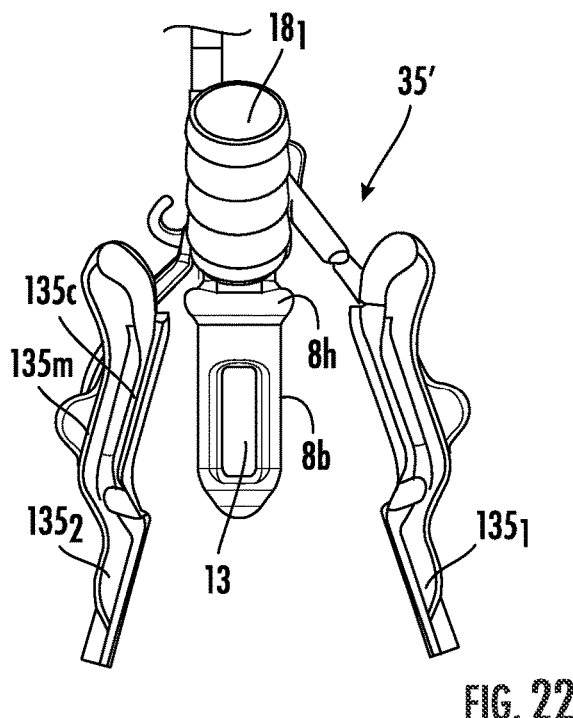
Figure 22C:
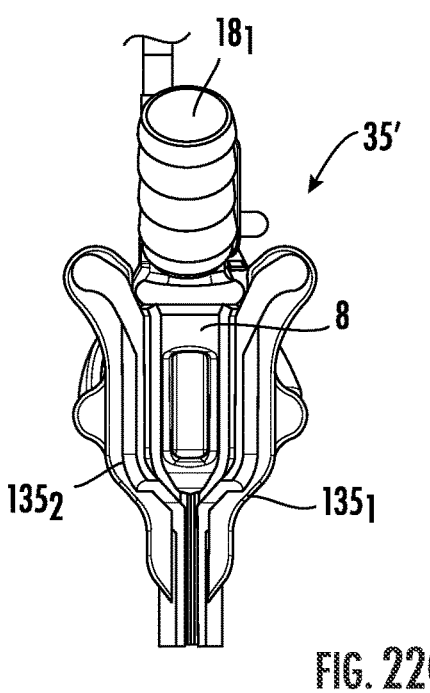
Figure 22D:
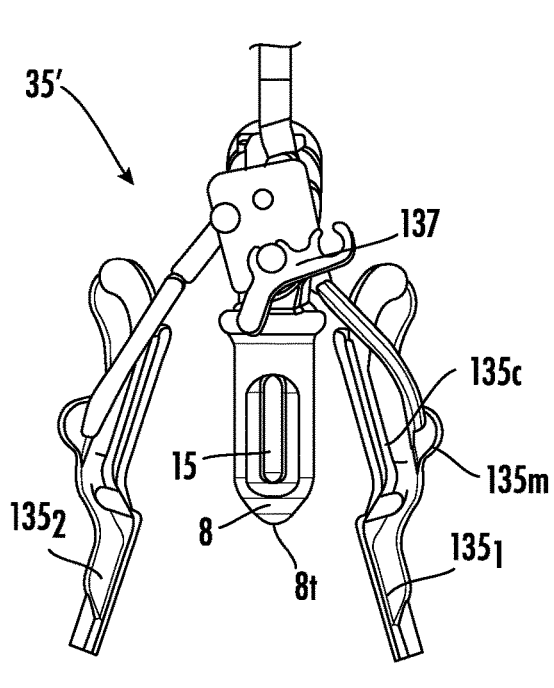
Figure 22E:
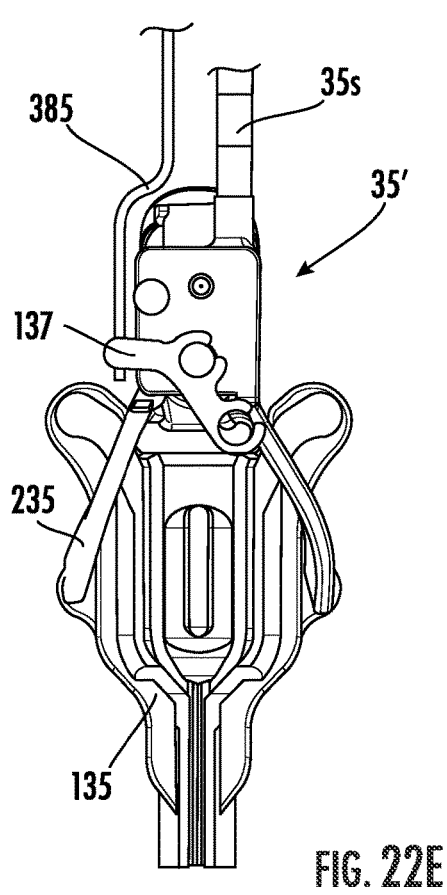
Figure 22F:
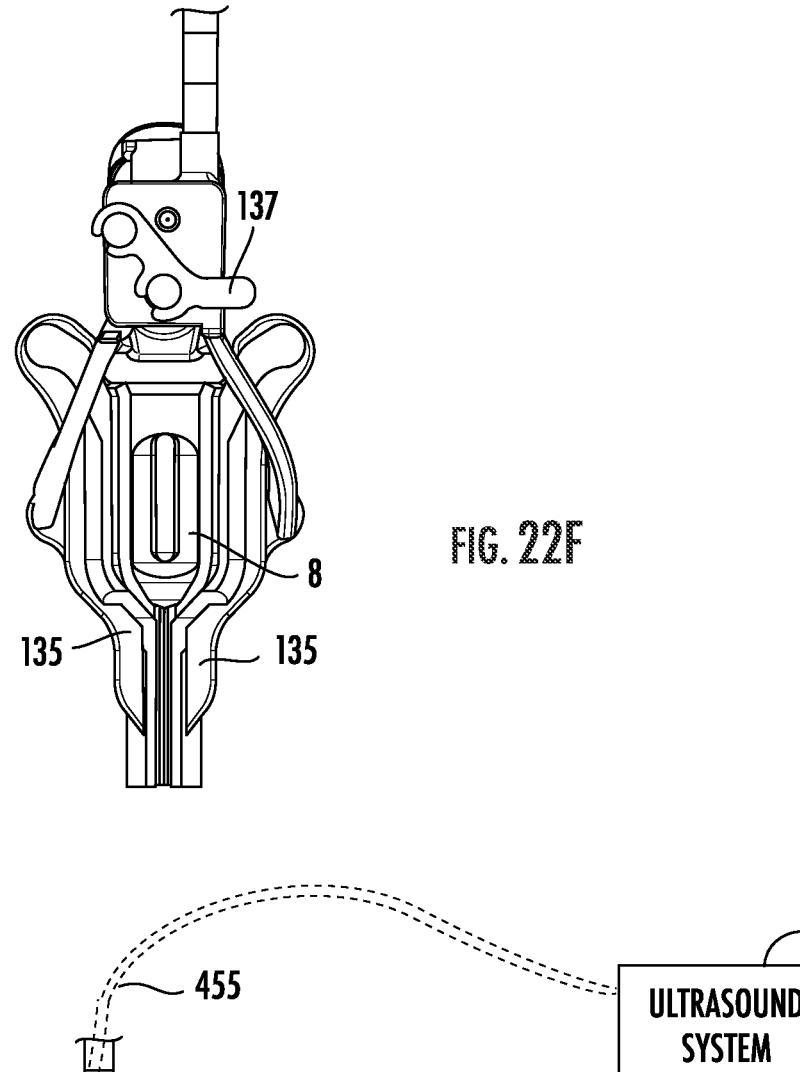
Figure 23:
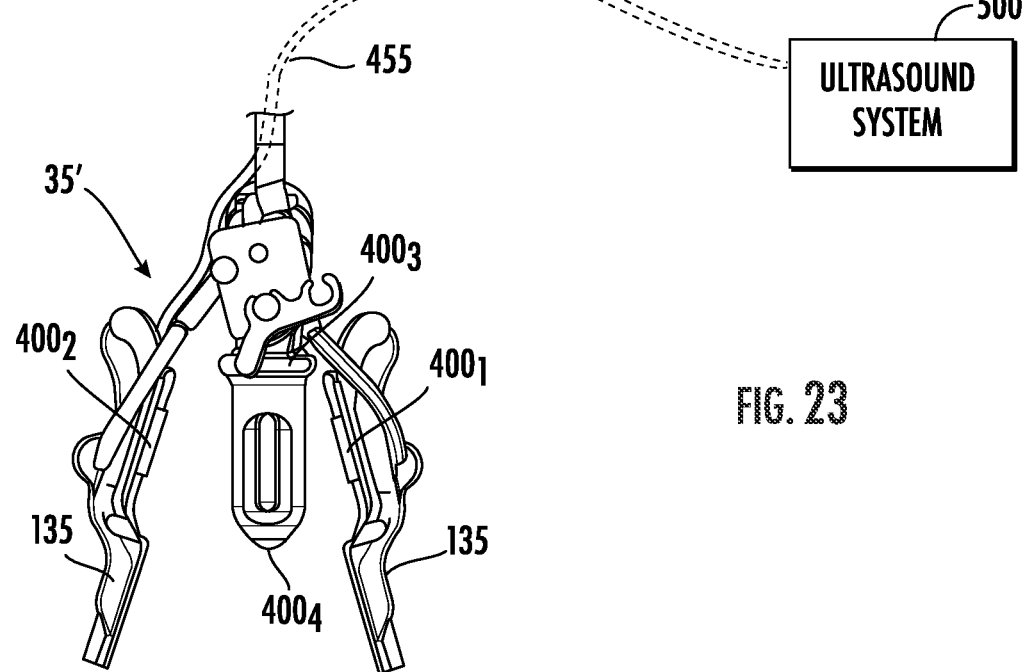
FIG. 23 shows the dual lumen cannula and clamp in an open position of the clamp and with example sites with ultrasound probes according to embodiments of the present invention.
Figure 24A:
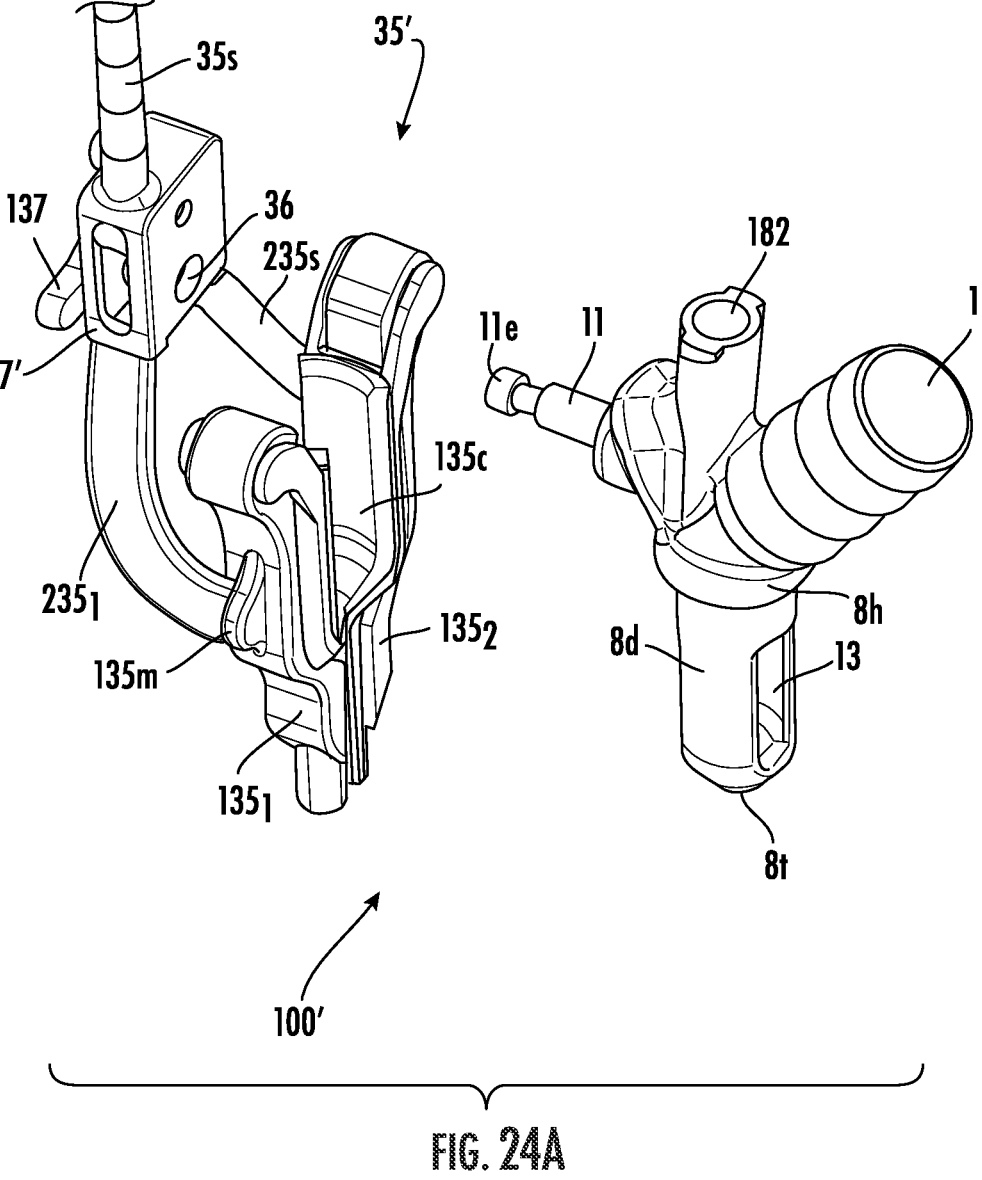
FIG. 24A is a partially exploded view of the clamp assembly and dual lumen cannula shown in FIG. 16 according to embodiments of the present invention.
Figure 24B:
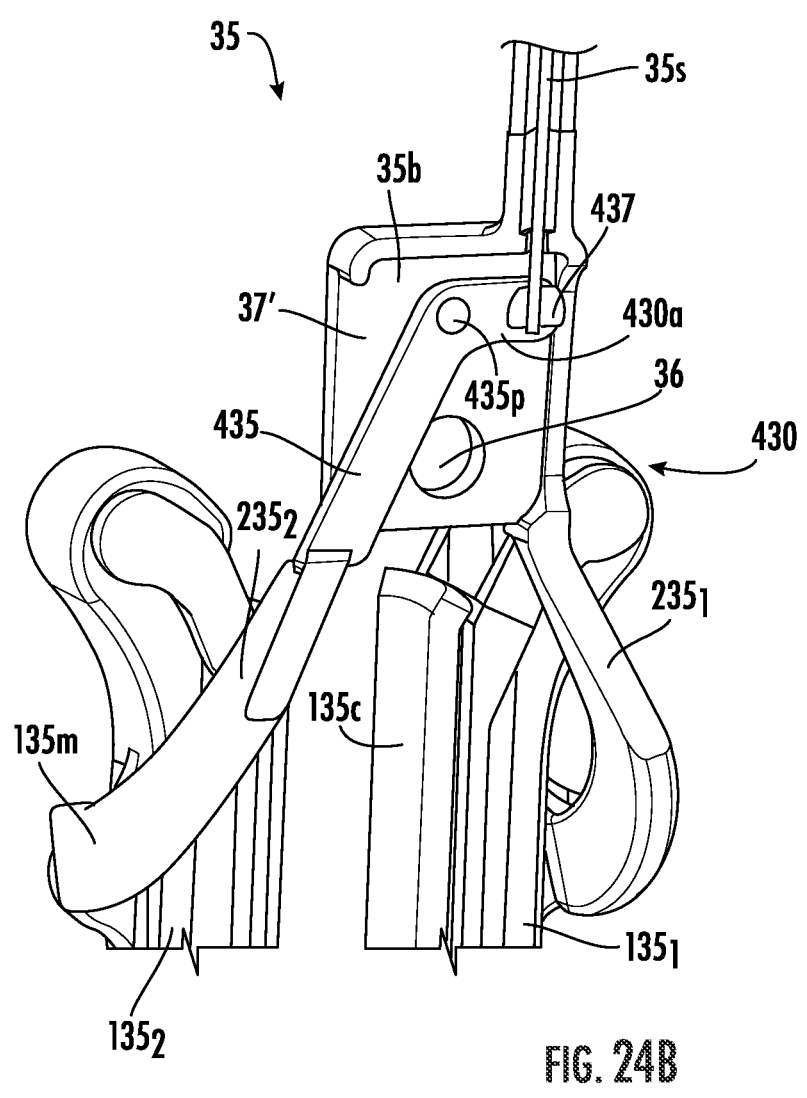
FIG. 24B is a partial section view of a clamp deployment assembly for the clamp assembly shown in FIG. 24A according to embodiments of the present invention.

The double lumen cannula 8 can have a distal end portion 8d that merges into a proximal end portion 8p. The distal end portion 8d is sized and configured to reside (entirely) within the vessel wall Aw of an aorta A. In some example embodiments, the distal end portion 8d that resides entirely within a vessel can have a length "d" that is in a range of about 0.5 cm to about 2.5 cm, depending on the vessel diameter. The double lumen cannula 8 can be provided in different sizes with different lengths "d" to accommodate different patient needs, including pediatric and/or gender-based sizing. The length "d" corresponds to a diameter or cross-sectional width of the aorta but can be within +/−10% of such a size, as long as the distal end 8d can define a closed segment across the vessel between upstream and downstream aortic compartments $A_1$, $A_2$ when a cooperating clamp 35 is applied to the distal end 8d of the double lumen cannula 8 with the vessel wall Aw of the aorta A therebetween (FIGS. 14,15).

The distal end portion 8d can have a closed tip 8t. The tip 8t can be tapered or curved to provide an atraumatic contact segment for the inner surface of the aortic wall thereat. The tip 8t can comprise a medical grade material that is more flexible, resilient and/or has a softer tactile structure than the unitary body 8b of the dual lumen cannula 8.

The double lumen cannula 8 can have a unitary body 8b that provides the tip 8t, the internal lumens 9, 10 of the distal end portion 8d and the respective lumen orifices 13, 15. The distal end portion 8d can have an internal partition wall 8w that extends longitudinally between the first and second lumens 9, 10 and provides the fluid isolation therebetween. The internal partition wall 8w is not required to bisect the distal end 8d of the double lumen cannula 8 and can be offset laterally and extend longitudinally to define the first and second lumens 9, 10 inside the distal end portion 8d of the double lumen cannula 8, so that the first lumen 9 can have a larger width and/or volumetric size than the second lumen 10.

The unitary body 8b can also be configured to provide the proximal end portion 8p of the double lumen cannula 8 which terminates outside but adjacent the aorta. The proximal end portion $8p$ of the double lumen cannula 8 can include first and second branches $18_1$, $18_2$.

The unitary body $8b$ can also define a hub $8h$ that has an increased lateral width relative to the distal end portion $8d$ of the double lumen cannula 8. The hub $8h$ can reside outside the aortic wall and beneath the first and second branches $18_1$, $18_2$. The hub $8h$ can provide a stop position with the outer surface of the vessel wall thereat.

The first branch $18_1$ is in fluid communication with the first lumen 9 and the second branch $18_2$ is in fluid communication with the second lumen 10. The first and second branches $18_1$, $18_2$ can connect to respective first and second conduits $18c_1$, $18c_2$ that can have increased flexibility relative to other portions of the double lumen cannula 8 such as, for example, the hub $8h$, the unitary body $8b$ and/or the distal end portion $8d$ of the double lumen cannula 8. The branches $18_1$, $18_2$ provide fluidly isolated fluid flow paths to and/or from the aorta of a patient that can be (selectively) used separately.

The second branch $18_2$ can merge into a connector 25 that couples the second branch $18_2$ to first and second tubes $19_1$, $19_2$. The first tube $19_1$ can be configured for the delivery of cardioplegia via the second lumen 10. The second tube $19_2$ can be configured for suction of air from the aorta via the second lumen 10, such as in medical procedures such as valve replacements where removing the air from the heart chambers is desired before the removal of a cross-clamp 35 (FIG. 6).

Figure 4:
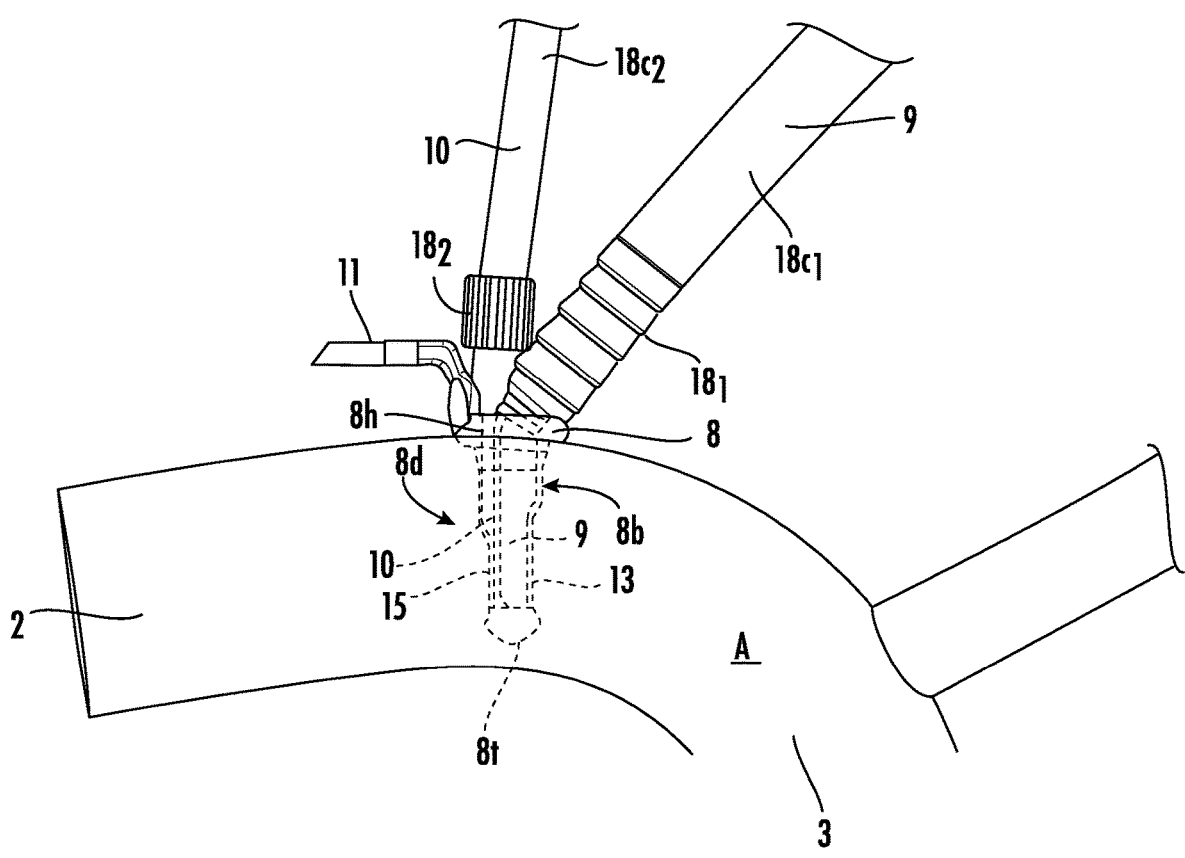
FIG. 4 is an enlarged lateral view of the double lumen cannula shown in FIG. 3, illustrating lumen orifices according to embodiments of the present invention.
Figure 5:
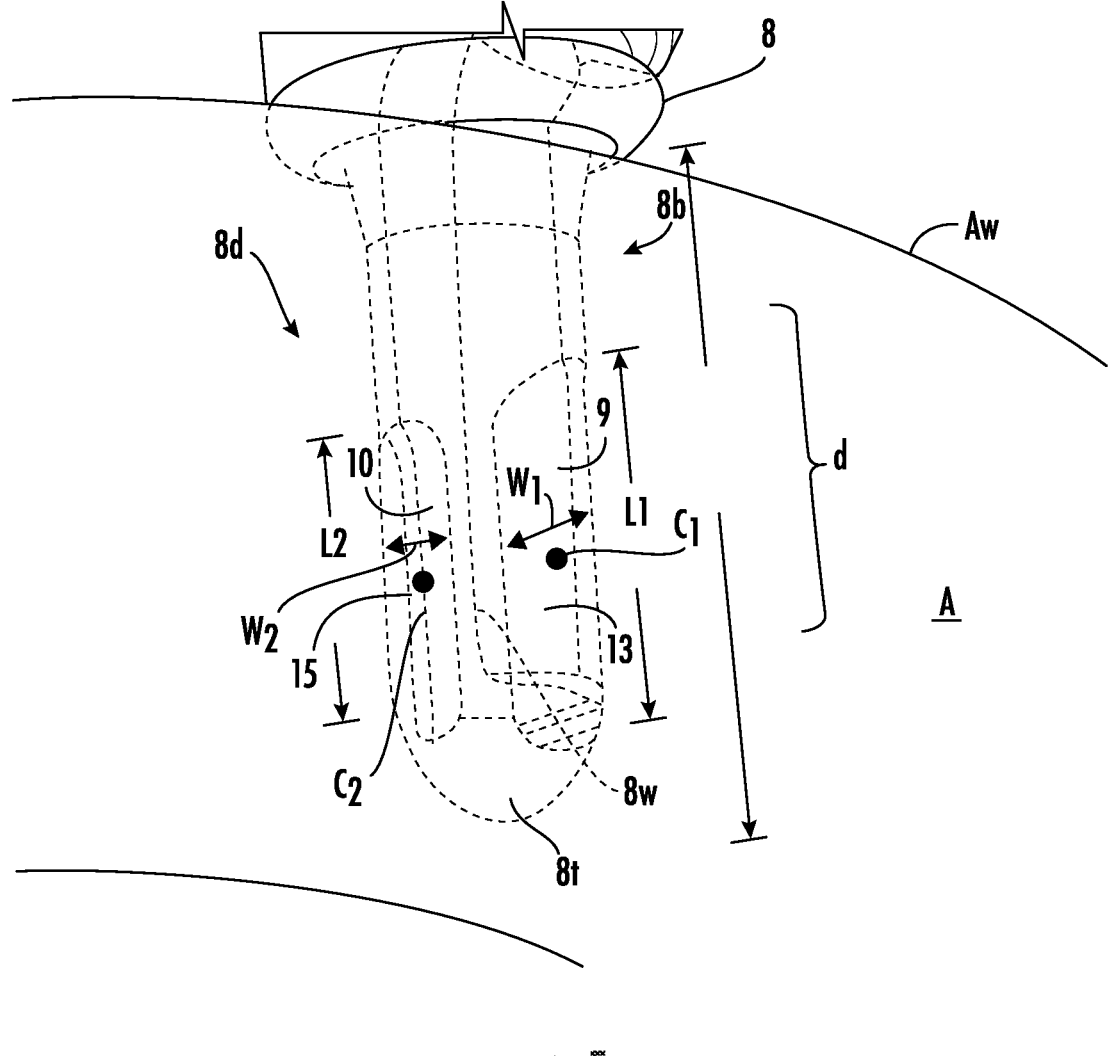
FIG. 5 is an enlarged side perspective view of a distal end portion of the dual lumen cannula shown in FIG. 4.

Referring to FIGS. 4 and 5, the double cannula 8 can be configured for arterial perfusion via lumen 9 and delivery of cardioplegia via lumen 10. The first orifice 13 for delivery of arterial flow can be relatively large, shown in FIG. 5 has extending greater than a major length (greater than 50%) of the distal end $8d$ of the double cannula 8 inside the aorta A and having a length $L_1$ and width $W_1$ that can be configured to reside medially in the aortic vessel, facing the distal ascending aorta. The orifice 15 configured for cardioplegia can be smaller than orifice 13 with a length $L_2$ and width $W_2$ that are both less than corresponding dimensions of the orifice 13. The orifice 15 can also be configured to reside (be positioned) medially in the vessel, facing the ascending aorta for coronary perfusion. A center $c_1$ of the length dimension of the first orifice 13 can reside above a center $c_2$ of the length dimension of the second orifice 15. The orifices 13, 15 can be configured to direct flow laterally rather than toward either inner wall surface of the aorta A. The medial position of the orifices 13, 15 inhibits and/or prevents the "sand blasting" effect described above. This feature can potentially reduce the incidence of stroke in cardiac surgery.

The distal end portion $8d$ of the dual/double lumen cannula 8 resides inside the aortic vessel A and the clamp assembly 35 couples to the distal end $8d$ of the double cannula 8 with the aortic wall Aw therebetween providing a mechanical sealing.

Figure 6:
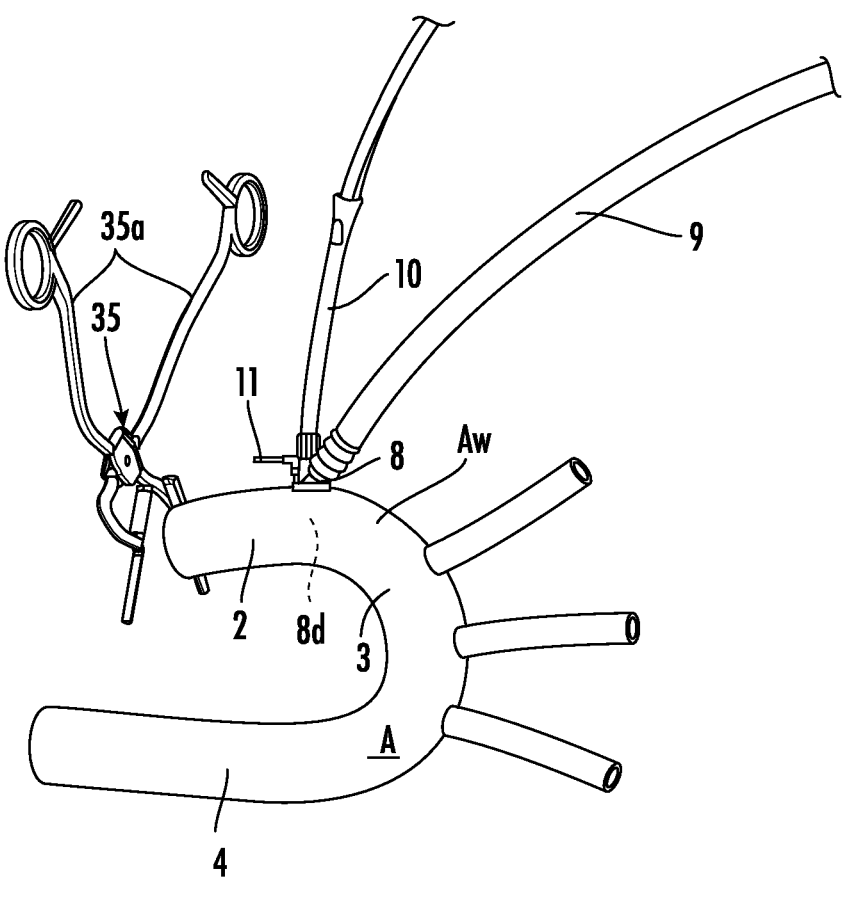
FIG. 6 is a side perspective view of the double lumen cannula shown in FIG. 3, placed in the aorta with a clamp separate from the double lumen cannula according to embodiments of the present invention.

Referring again to FIGS. 2-5, the double lumen cannula 8 can have a coupling pin 11 configured to provide alignment and or an interface for assembly with a (cross) clamp assembly 35 (FIG. 6). The coupling pin 11 can extend laterally outwardly from the distal end portion $8d$ of the double cannula 8, typically at or above the hub $8h$, external to but adjacent the aorta A. The coupling pin 11 can extend in a direction facing a defined direction associated with either the ascending aorta 2 or the descending aorta 4 and defining an orientation of the distal end portion $8d$ of the double lumen cannula 8 with the orifices 13, 15 correctly positioned to face the correct direction for ease of positioning in a correct orientation during surgery.

Turning now to FIGS. 6, 7A, 8 and 9, an example clamp assembly 35 is shown. The clamp assembly 35 can be a separate component from the double lumen cannula 8 and can be configured to cooperate with the distal end portion $8d$ of the double lumen cannula 8 to seal the two aortic compartments A1, A2 as discussed above. The clamp assembly 35 can have an actuator $35a$ shown as handle members that direct the clamp assembly 35 to move between open and closed positions. The clamp assembly 35 can have an aperture 36 in a center of a hinge segment $35h$ that slidably receives the coupling pin 11.

The clamp assembly 35 can have first and second clamp arms $135_1$, $135_2$ that can be coupled to the hinge segment $35h$ via arcuate leg segments $235_1$, $235_2$. The arcuate leg segments $235_1$, $235_2$ can attach to a medial segment $135m$ of respective clamp arms $135_1$, $135_2$ and position the clamp arms $135_1$, $135_2$ away from the hinge segment $35h$ toward the distal end portion $8d$ of the double lumen cannula 8.

Figure 9:
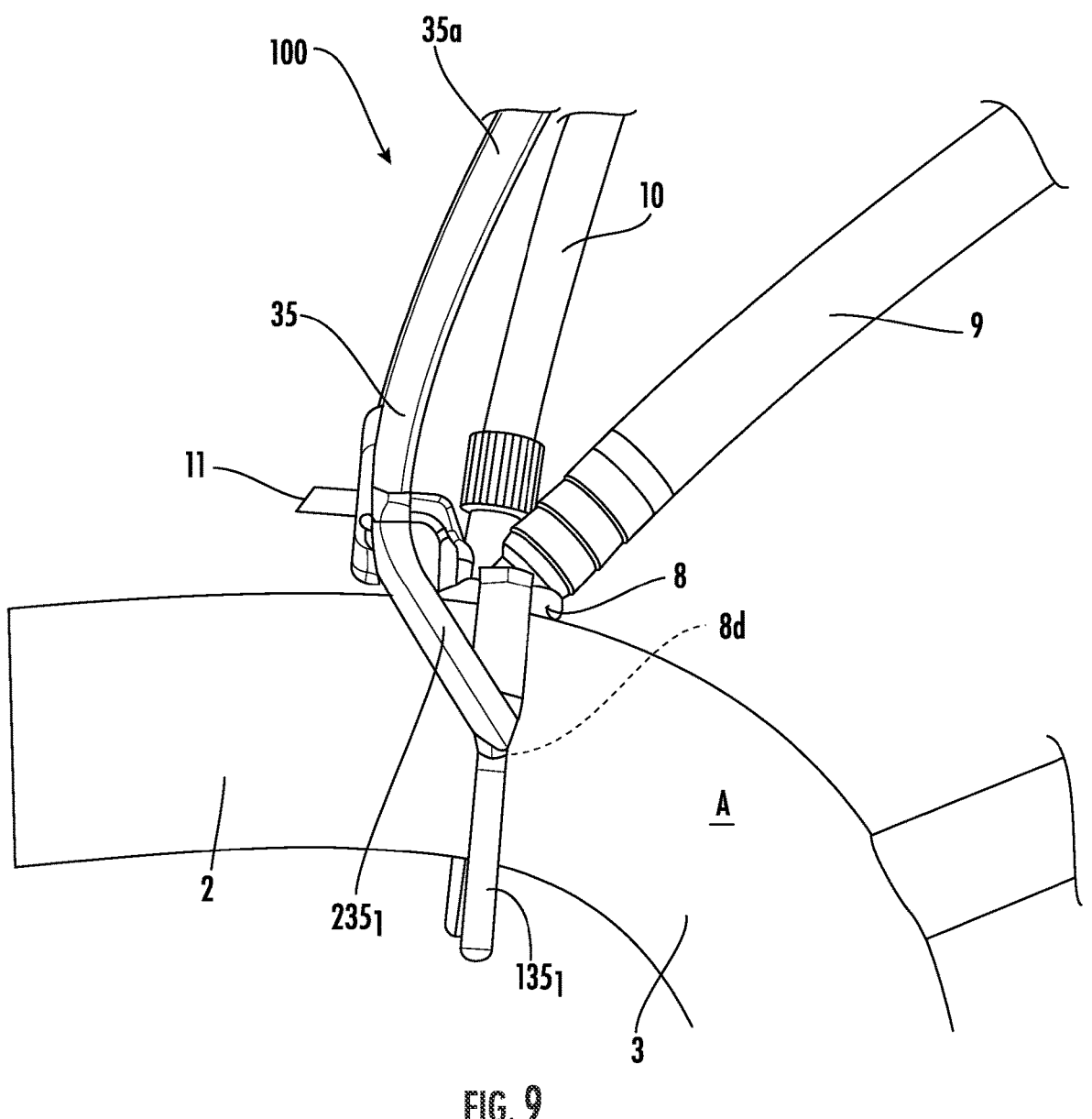
FIG. 9 is a side view of the assembly with the clamp aligned with and coupled to the double lumen cannula according to embodiments of the present invention.
Figure 13:
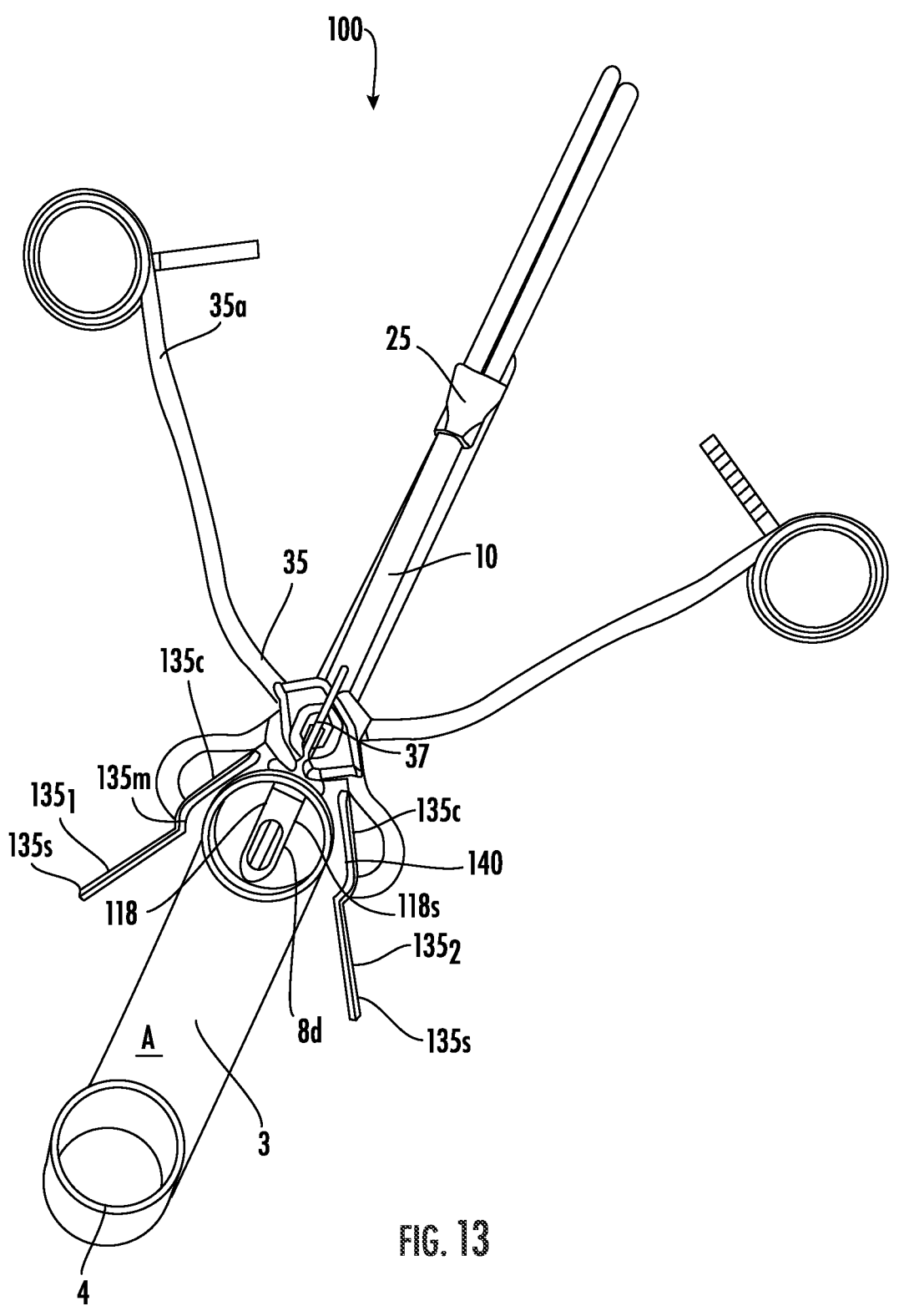
FIG. 13 is a side perspective view of the clamp and double lumen cannula with the aorta shown in partial section view to show alignment of the clamp halves with the double lumen cannula according to embodiments of the present invention.

Referring to FIGS. 9, 13, and 14, the clamp assembly 35 and the double lumen cannula 8 cooperate to provide a clamp and double lumen cannula assembly 100. FIG. 13 shows the clamp assembly 35 in position but with clamp arms $135_1$, $135_2$ open while FIG. 14 shows the clamp assembly with the clamp arms $135_1$, $135_2$ closed against the double lumen cannula 8 with the aortic wall therebetween.

Figure 12:
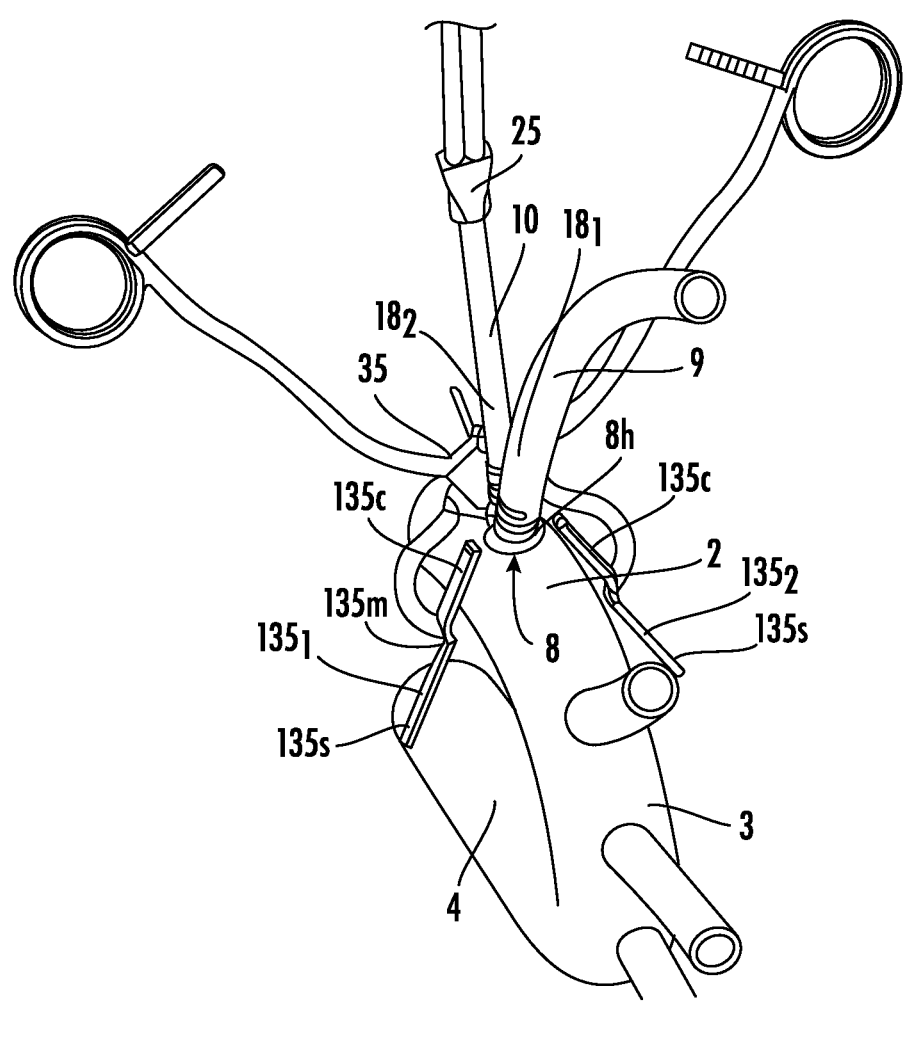
FIG. 12 is a top, side perspective view of the pair of clamp halves positioned away from the wall of the aorta, with the clamp interlocked with the double lumen cannula before deploying to the clamping position according to embodiments of the present invention.

As shown in FIGS. 12 and 13, the clamp arms $135_1$, $135_2$ can have a curvilinear segment $135c$ that merges into a straight linear segment $135s$ under the medial segment $135m$.

As shown in FIGS. 14 and 15, the straight linear segments $135s$ of each of the clamp arms $135_1$, $135_2$ can abut under the distal end portion $8d$ of the cannula 8 outside the aorta in the closed position.

Referring to FIG. 13, the curvilinear segment $135c$ of a respective clamp arm can have the same curvature or contour as the outer surface $118s$ and/or outer wall 118 of the distal end portion $8d$ of the dual lumen cannula 8 facing the respective curvilinear segment $135c$.

Figures 7A, 7B:
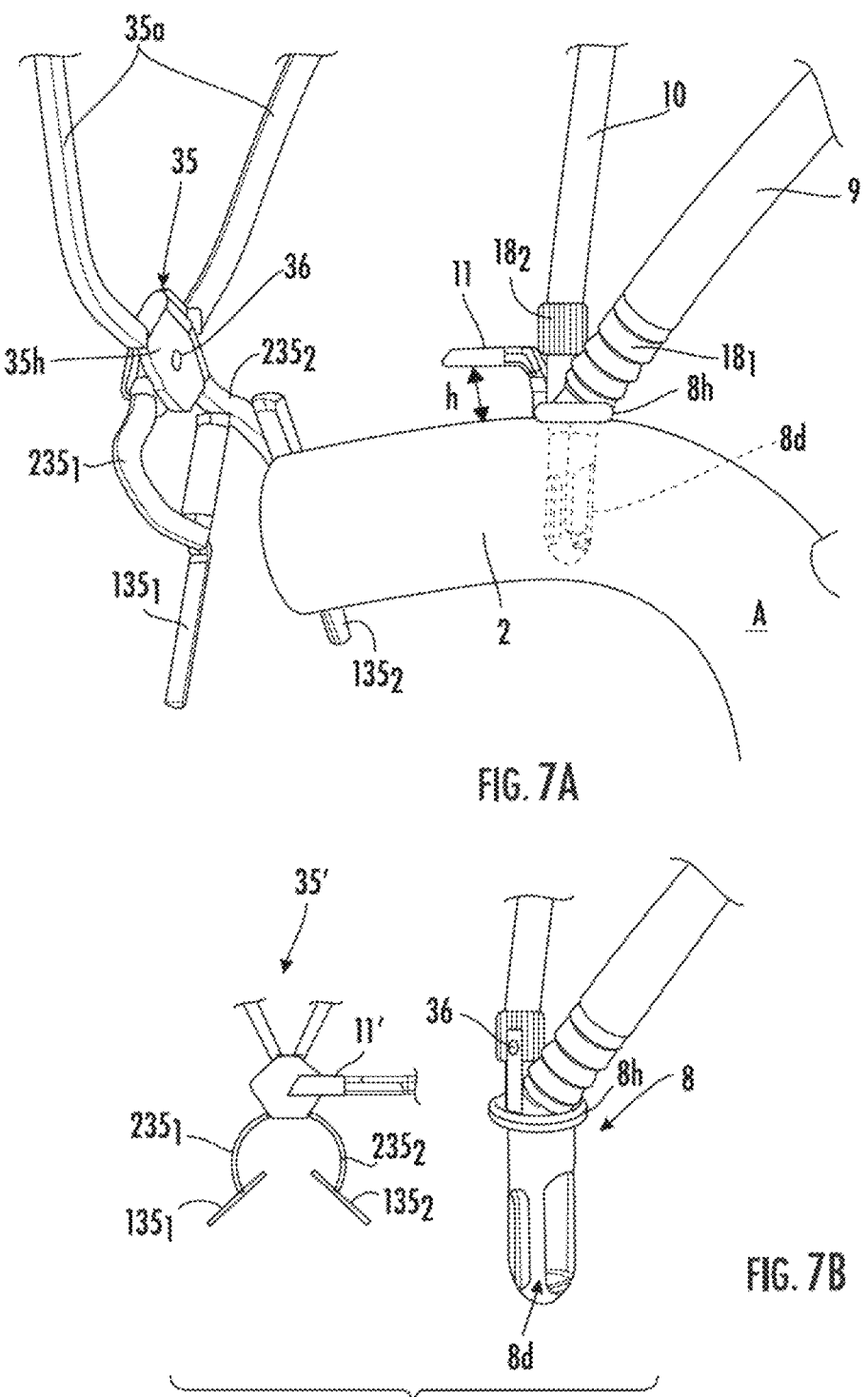
FIG. 7A is an enlarged side perspective view of the double lumen cannula and clamp shown in FIG. 6.
FIG. 7B is a schematic illustration of another embodiment of the double lumen cannula and clamp.
Figure 8:
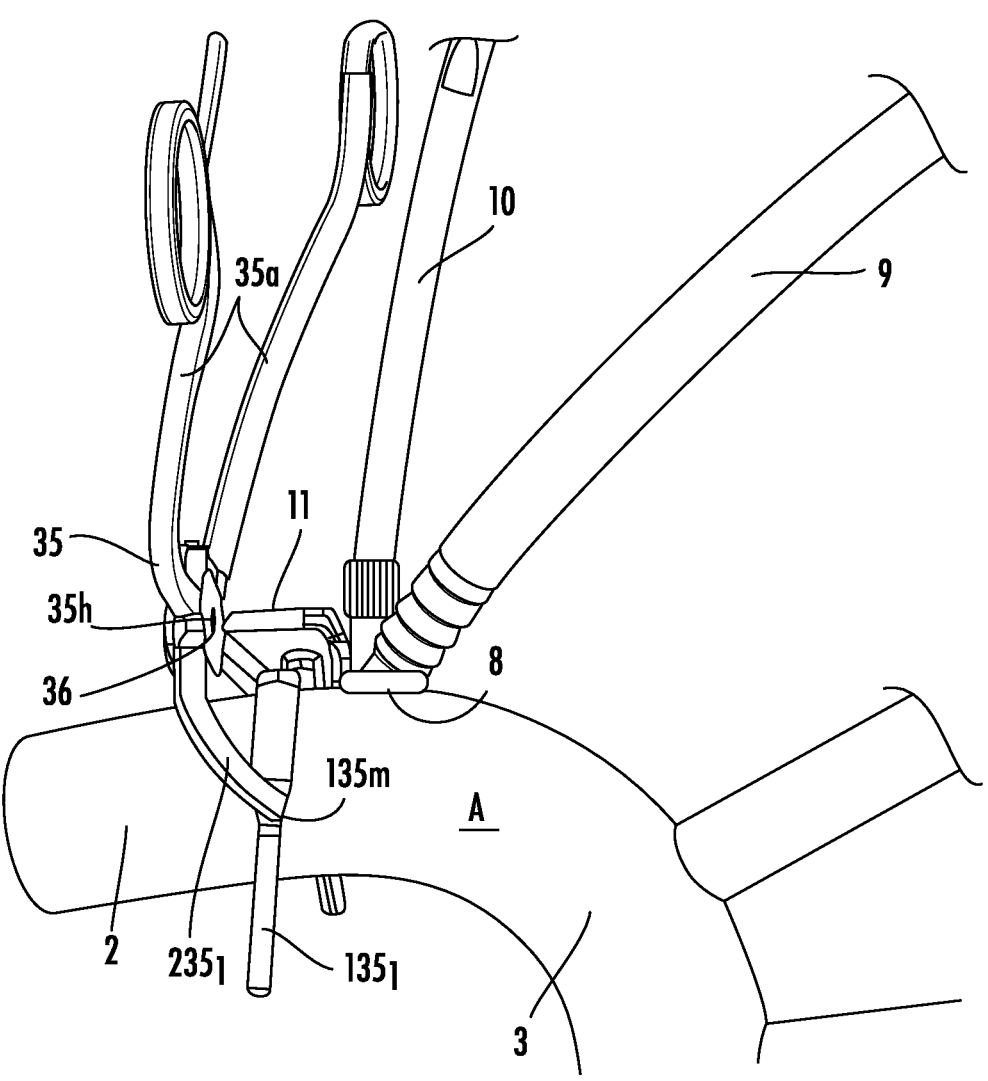
FIG. 8 is a side view of the clamp shown in FIG. 6 with the clamp in open position next to the cannula according to embodiments of the present invention.

Referring to FIG. 7A, the coupling pin 11 and/or aperture 36 can reside a distance "h" above an outer wall of the vessel wall Aw, in position in the body, typically closely adjacent the outer wall for structural enforcement and/or for providing a positionally stable attachment relative to the target aortic region. The distance "h" can be in a range of 0.1 mm to 25 mm, in some embodiments.

FIG. 7B illustrates that the clamp assembly 35' can include the coupling pin 11' and the double lumen cannula 8 can include a coupling member 136 with an aperture 36' that slidably receives the coupling pin 11'. More than one coupling pin 11, 11' can be used. One coupling pin 11' can be provided by the clamp assembly 35 and one coupling pin 11 can be provided by the double lumen cannula 8. Other coupling and interlocking configurations may be used.

The clamp assembly 35 is configured to have sufficient mobility to allow the first and second clamp arms $135_1$, $135_2$ of the clamp assembly 135 to pass externally about the aorta A and align with the internal distal end portion $8d$ of the double lumen cannula 8.

After the insertion of the cannula 8 and institution of cardiopulmonary bypass, the clamp arms $135_1$, $135_2$ of the clamp assembly 35 are positioned on each side of the aorta, the front wall and back wall. The clamping maneuver requires careful placement of the clamp assembly 35 aiming to close against an entire aortic circumference without causing damage to the surrounding structures.

Figure 10:
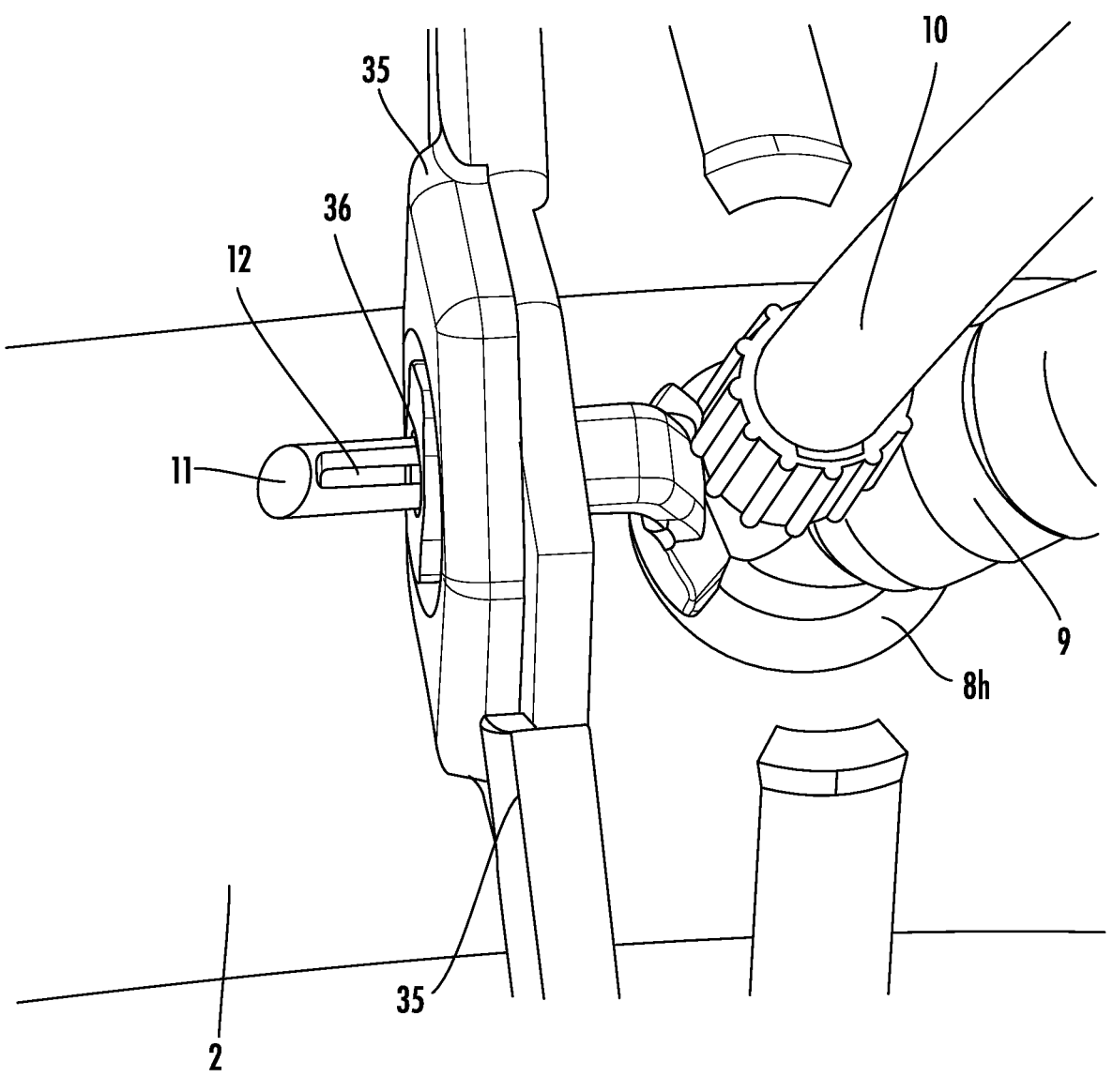
FIG. 10 is an enlarged top perspective view of the clamp and double lumen cannula with a groove in an alignment pin for interlocking the components according to embodiments of the present invention.
Figure 11:
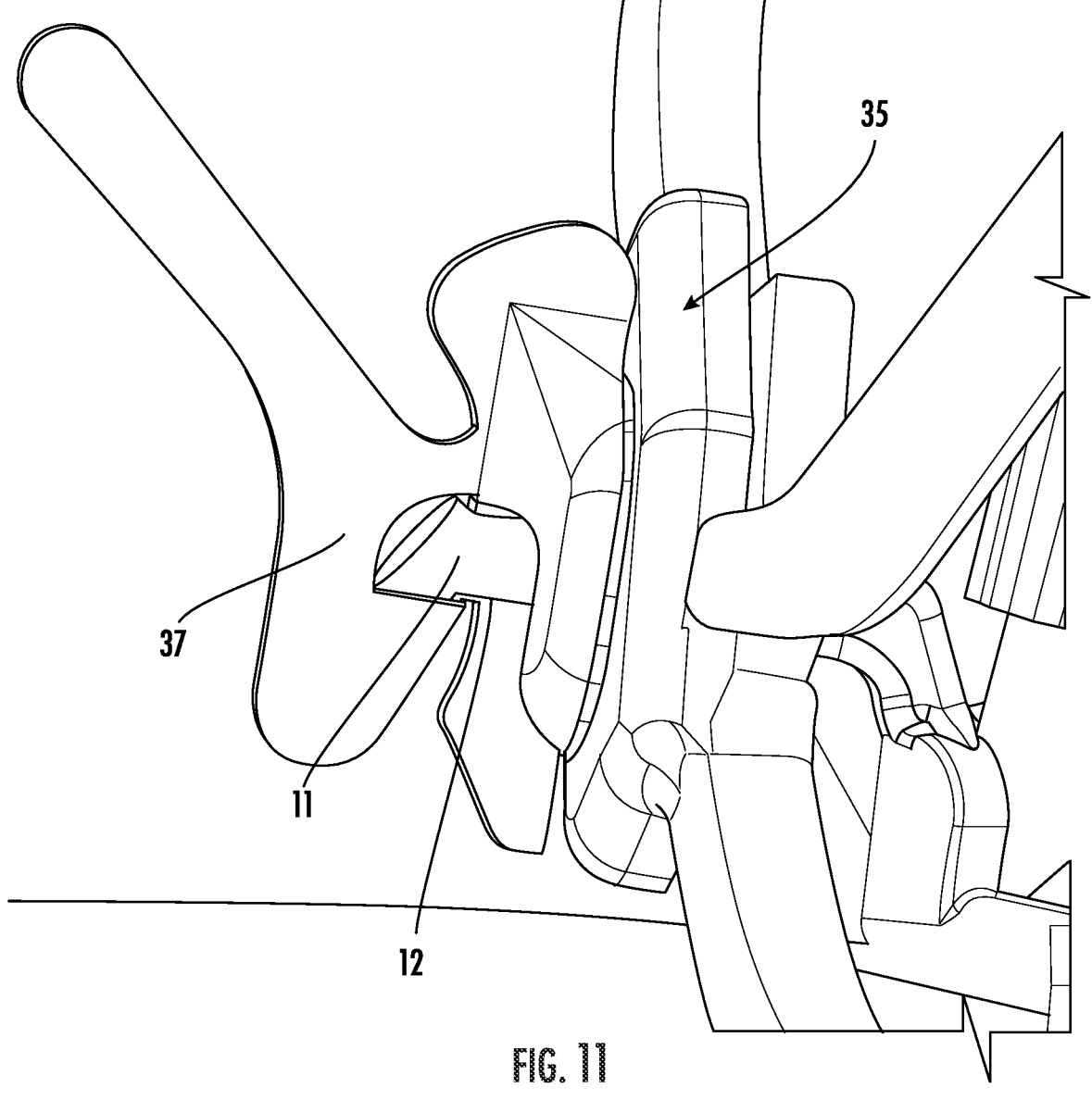
FIG. 11 is an enlarged top, side perspective view of the clamp and double lumen cannula interlocked to inhibit/prevent movement and accidental dislodgment of the clamp according to embodiments of the present invention.

Referring to FIGS. 9-11, the coupling between the double lumen cannula 8 and the clamp assembly 35 provides the occlusion of the aorta A. However, the coupling should be configured so as to not interfere with the opening and closing of the clamp arms $135_1$, $135_2$. In some embodiments, the coupling pin $11$ of the double lumen cannula $8$ slidably extends through the opening $36$ in the center of hinging segment (a hinging point) common to the two clamp arms $135_1$, $135_2$ of the clamp assembly $35$. A lock member $37$ can be deployed or attached to the coupling pin $11$ to lock the double lumen cannula $8$ and the clamp assembly $35$ together at a desired location about and in the aorta A.

The clamp assembly $35$ is approximated and the opening $36$ in the center of the hinge segment $35h$ of the clamp assembly $35$ is aligned with the coupling pin $11$ on the double lumen cannula $8$. The closing of the clamp arms $135_1$, $135_2$ of the clamp assembly $35$ can only be performed once the clamp assembly $35$ is in its final position relative to the aorta and the double lumen cannula $8$. Thus, in some embodiments, the clamp assembly $35$ is slid onto the locking pin $11$ and locked into position using the slot $12$ and the lock member $37$ for interlocking and final assembly between the clamp assembly $35$ and double lumen cannula $8$, then allowing the clamp arms to close against the aortic vessel wall segments with the distal end portion $8d$ of the double lumen cannula $8$ therebetween.

FIG. $11$ shows the clamp $35$ assembly and the double lumen cannula $8$ interlocked using lock member $17$ to prevent movement and accidental dislodgment of the clamp assembly $35$. FIGS. $12$ and $13$ show the clamp assembly $35$ with the clamp arms $135_1$, $135_2$ in an in open position, with the clamp assembly $35$ interlocked with lock member $17$ in the lock position immediately before clamp maneuver (closing of the clamp arms $135_1$, $135_2$).

FIGS. $14$ and $15$ illustrate the clamp assembly $35$ in a closed position. clamp arm $135_1$, $135_2$, adjacent the distal end portion $8d$ of the dual lumen cannula $8$, can comprise curvilinear segments $135c$ and have a common curvature as the external surface $118s$ of the cannula wall $118$ allowing interposition of the aortic wall Aw between the surfaces.

Referring to FIG. $13$, the inner facing surfaces $140$ can be smooth with gradual transition to prevent any injury to the aortic wall Aw. The inner facing surfaces $140$ can include a medical grade material, such as a coating or insert, that provides increased resilience and/or a softer tactile contact surface relative to the outer facing surface of the clamp arms $135_1$, $135_2$.

Referring now to FIGS. $16$, $17$, $18A$-$18D$, $19A$, $19B$, $20A$-$20E$, $21A$ and $21B$, a minimally invasive embodiment of the clamp and double lumen cannula assembly $100'$ is shown. In this example embodiment, an elongate shaft $35s$ connects the externally accessible actuator $35a'$ to a pin $335$ that moves longitudinally to direct a clamp deployment assembly $435$, located adjacent the clamp assembly $35''$, to extend or retract the clamp arms $135_1$, $135_2$. The shaft $35s$ can be rigid, semi-rigid (having sufficient structural rigidity to retain it shape without support), or flexible.

Referring to FIGS. $16$ and $20C$, for example, the lock member $37'$ can comprise a lever $137$ that is configured to pivot between locked and unlocked positions. The lever $137$ can have at least one aperture $137a$ that can couple to at least one projecting stop member $237$.

The clamp deployment assembly $435$ can be configured to move longitudinally in response to input from the pin $335$ relative to the clamp assembly $35''$ to pivot the clamp arms $135_1$, $135_2$ to move between the open and closed (clamped) positions.

In some embodiments, the clamp arms $135_1$, $135_2$ that compress the aorta has a softer inner facing surface $140$ relative to an outer facing surface or outer wall of the clamp arms $135_1$, $135_2$ to inhibit and/or prevent injury of the vessel wall.

The clamp assembly $35$, $35'$, $35''$ can be provided in at least two different sizes, for different size patients and/or considering dilated or aortic aneurysm.

FIGS. $22A$-$22F$ are additional views of the assembly shown in FIG. $16$. FIGS. $22A$ and $22B$ show the clamp $35'$ in an unclamped orientation and the lock $37'$ and associated lever $137$ in an unlocked state. FIG. $22E$ shows the clamp $35'$ closed and the lock $37'$ unlocked. FIG. $22E$ also shows that a cable $385$ can be attached to the lever $137$ to allow for minimally invasive access for a user to actuate the lock lever $137$. FIG. $22F$ shows the clamp $35'$ closed and locked with the lever $137$ pivoted to a closed/locked position according to embodiments of the present invention.

FIG. $24A$ illustrates the surgical device $100'$ with the clamp assembly $35'$ aligned with the dual lumen cannula $8$ with the locking/alignment pin $11$ aligned with an aperture $36$ in a body of the clamp assembly $35'$ under the elongate shaft $35s$. The free end portion $11e$ of the pin $11$ can engage the locking lever $137$.

FIG. $24B$ illustrates that the clamp assembly can include a deployment assembly $430$ (which can also be described as an actuation assembly) with a clamp arm actuator $430a$ that can include an internal lever $435$ that is pivotably coupled to the body $35b$ of the clamp assembly $35'$ that can be above and vertically aligned with the aperture $36$ that receives the pin $11$. The elongate shaft $35s$ can be coupled to the lever $435$ at an end portion $437$ of the lever $435$, which can also be attached to the other clamp arm thereat, to direct both of the clamp arms $135_1$, $135_2$ to concurrently open and close. The actuation assembly $430a$ can take other forms to open and close the clamp arms.

The clamp handle of the clamp actuator $35a$, $35a'$ is a standard hard handle, however flexible clamp mechanism or combination of standard and flexible can be used in this case.

FIG. $23$ illustrates that an ultrasound probe $400$ can be integrated with or attached to the clamp assembly $35$ or the double lumen cannula $8$ to allow for visualization of a desired location to place the cannula $8$ and clamp assembly $35$ and to allow for visualization of a suitable location to place the distal end portion $8d$ of the cannula $8$. FIG. $23$ illustrates example attachment locations (1)-(4) and the use of a cable $455$ to connect the ultrasound probe $400$ to an external ultrasound system $500$ with a display.

The ultrasound probe $400$ can also or alternatively provide visualization of the alignment and/or closure of the clamp arms $135_1$, $135_2$ to avoid applying an unduly large clamping force against the vessel wall of the aorta. Pressure sensors, optical or proximity sensors or other sensors may also be used to provide feedback to a clinician regarding the position of the clamp assembly $35$, $35'$ relative to the distal end $8d$ of the cannula $8$ to precisely indicate when the clamp is fully closed/clamped and/or regarding pressure applied by the clamp arms to the vessel wall and/or the distal end portion of the double lumen cannula $8$. The use of the ultrasound probe $400$ and/or miniature sensors can help avoid disrupting or breaking plaque off the inner wall of the aorta. The ultrasound probe $400$ can be a miniaturized probe and can be placed on either of the sides of the clamp assembly $35$, $35'$ or on the double lumen cannula $8$, outside the aorta, such as adjacent the hub $8h$ and/or facing the clamp assembly/clamp arms $135_1$, $135_2$.

FIG. $25$ illustrates example actions that can be carried out during a surgical procedure. A dual lumen cannula comprising a distal end portion configured to reside inside an aorta of a patient is provided. The distal end portion comprises a first lumen and a second lumen in fluid isolation (block 600). The distal end portion of the dual lumen cannula is positioned inside the aorta of the patient (block 610). An outer wall of the aorta is clamped against the distal end portion of the dual lumen cannula to separate the aorta into two fluidly isolated compartments (block 620). Cardioplegic solution is introduced into the patient via a lumen orifice of the second lumen facing an ascending aorta segment of the aorta for proximal delivery of cardioplegia to the coronary arteries (block 630). Arterial perfusion is provided via a lumen orifice of the first lumen facing a descending segment of the aorta for distal arterial body perfusion (block 640).

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention. Therefore, it is to be understood that the foregoing is illustrative of the present invention and is not to be construed as limited to the specific embodiments disclosed, and that modifications to the disclosed embodiments, as well as other embodiments, are intended to be included within the scope of the invention.

That which is claimed:

1. A cardiothoracic surgical device comprising:
a dual lumen cannula comprising a distal end portion with a tubular body configured to reside inside an aorta of a patient and that extends in a straight longitudinal direction to position a bottom of the tubular body in line with and below a top of the tubular body, wherein the tubular body comprises an outer wall surrounding a first lumen and a second lumen that are in fluid isolation from each other, wherein the first lumen comprises a first orifice extending through the outer wall that is configured to face a first direction inside the aorta, and wherein the second lumen comprises a second orifice extending through the outer wall that is configured to face a second direction that is different than the first direction inside the aorta with the first orifice and the second orifice being circumferentially spaced apart;
a first conduit that is coupled to the first lumen and that is configured to extend outside the aorta and has a length sufficient to extend externally from a patient;
a second conduit that is coupled to the second lumen and that is configured to extend outside the aorta with a length sufficient to extend externally from the patient; and
a clamp assembly detachably coupled to the dual lumen cannula and configured with first and second clamp arms that are configured to align with the tubular body of the dual lumen cannula, wherein the first and second clamp arms are configured to clamp opposing sides of a vessel wall of the aorta between the tubular body and the first and second clamp arms to thereby compress the vessel wall against the outer wall of the tubular body and thereby provide first and second fluidly isolated segments of the aorta,
wherein at least one of the first conduit and the second conduit extends from the tubular body at a position that is outside of and laterally spaced apart from the clamp assembly, wherein the tubular body at the distal end portion is defined by a unitary body structure that has an internal solid wall that extends across the tubular body to the outer wall to separate the first and second lumens and that extends in a longitudinal direction between the first and second lumen, and wherein the first orifice and the second orifice each have a center, with the center of the first orifice positioned above the center of the second orifice,
wherein the unitary body structure has increased rigidity relative to the first and second conduits, and
wherein, when coupled to the tubular body and in position to move to a closed position, the clamp assembly comprises a hinge segment with a hinge that is laterally offset from an axially extending centerline of the tubular body.

2. The cardiothoracic surgical device of claim 1, wherein the dual lumen cannula further comprises a coupling pin that is configured to extend outside and adjacent to the aorta and into or through an aperture in the clamp assembly with the aperture positioned under the hinge to thereby provide the detachable coupling, and wherein the coupling pin is a single coupling pin configured to laterally slidably receive the clamp assembly to provide the detachable coupling, and wherein the single coupling pin is positioned above and laterally outward from the tubular body in a direction associated with either an ascending aorta or a descending aorta and define an alignment orientation of the tubular body.

3. The cardiothoracic surgical device of claim 2, wherein the coupling pin and the aperture have a fixed position when coupled together, and wherein the first and second clamp arms are configured to pivot between open and closed positions while the coupling pin is in the fixed position and in the aperture of the clamp assembly.

4. The cardiothoracic surgical device of claim 1, wherein the tubular body has a tapered closed tip that is configured to face and abut an inner surface of the vessel wall of the aorta.

5. The cardiothoracic surgical device of claim 1, wherein the first conduit has a greater inner diameter than the second conduit.

6. The cardiothoracic surgical device of claim 1, wherein the second conduit merges into a connector interface that couples first and second tubes to the second conduit thereby allowing separate fluid channels for venting and introducing cardioplegia solution, respectively.

7. The cardiothoracic surgical device of claim 1, wherein the tubular body has a proximal end with a hub that comprises a connector interface with first and second branches that are in fluid communication with respective first and second lumens, and wherein the hub and the connector interface are configured to reside outside and adjacent the vessel wall of the aorta.

8. The cardiothoracic surgical device of claim 1, wherein the distal end portion comprises an internal solid wall that extends radially across and along the tubular body between the first lumen and the second lumen, and wherein the first orifice has a longer longitudinal extent than the second orifice and with part of the first orifice longitudinally aligned with part of the second orifice.

9. The cardiothoracic surgical device of claim 1, wherein the distal end portion has a hub that is attached or integral to the tubular body and that is configured to be external to the aorta, wherein the tubular body is below the hub and is configured to reside entirely in the aorta, and wherein the hub comprises a first branch in fluid communication with the first lumen and a second branch in fluid communication with the second lumen, wherein the first and second branches extend above the hub and terminate adjacent the hub, and wherein at least one of the first and second branches angle outward from an axially extending centerline of the tubular body in an upward direction with the first branch connected to the first conduit and the second branch connected to the second conduit.

10. The cardiothoracic surgical device of claim 1, wherein the unitary body structure has a top with a connection interface defining first and second branches, at least one of which angles outward in an upward direction away from the tubular body, and wherein the first branch is in fluid communication with and couples to the first conduit and the second branch is in fluid communication with and couples to the second conduit.

11. The cardiothoracic surgical device of claim 1, wherein the clamp assembly comprises a deployment assembly coupled to an elongate shaft, and wherein the elongate shaft is coupled to an actuator that directs the deployment assembly to close the first and second clamp arms against the distal end portion of the dual lumen cannula.

12. The cardiothoracic surgical device of claim 1, further comprising a lock member that is configured to a allow a user to lock the clamp assembly to the dual lumen cannula and that is configured to allow the user to unlock the clamp assembly from the dual lumen cannula whereby the clamp assembly is laterally slidably detachable from the dual lumen cannula.

13. The cardiothoracic surgical device of claim 1, wherein the clamp assembly also comprises a first arcuate leg that extends outward from the first clamp arm and that is connected to a medial segment of the first clamp arm and a second arcuate leg that extends outward from and that is connected to a medial segment of the second clamp arm, and wherein, in a closed position, the first and second clamp arms are aligned with the tubular body at the distal end portion of the dual lumen cannula.

14. The cardiothoracic surgical device of claim 1, further comprising an ultrasound probe coupled to the clamp assembly and/or coupled to the dual lumen cannula.

15. The cardiothoracic surgical device of claim 1, wherein the first and second clamp arms comprise a material on an inner facing segment that is configured to clamp against the aorta that has less rigidity than another material of the first and second clamp arms.

16. A cardiothoracic surgical device comprising:
a dual lumen cannula comprising a distal end portion with a tubular body configured to reside inside an aorta of a patient and that extends in a straight longitudinal direction to position a bottom of the tubular body in line with and below a top of the tubular body, wherein the tubular body comprises an outer wall surrounding a first lumen and a second lumen that are in fluid isolation from each other, wherein the first lumen comprises a first orifice extending through the outer wall that is configured to face a first direction inside the aorta, and wherein the second lumen comprises a second orifice extending through the outer wall that is configured to face a second direction that is different than the first direction inside the aorta with the first orifice and the second orifice being circumferentially spaced apart;
a first conduit that is coupled to the first lumen and that is configured to extend outside the aorta and has a length sufficient to extend externally from a patient;

a second conduit that is coupled to the second lumen and that is configured to extend outside the aorta with a length sufficient to extend externally from the patient; and
a clamp assembly detachably coupled to the dual lumen cannula and configured with first and second clamp arms that are configured to align with the tubular body of the dual lumen cannula, wherein the first and second clamp arms are configured to clamp opposing sides of a vessel wall of the aorta between the tubular body and the first and second clamp arms to thereby compress the vessel wall against the outer wall of the tubular body and thereby provide first and second fluidly isolated segments of the aorta,
wherein at least one of the first conduit and the second conduit extends from the tubular body at a position that is outside of and laterally spaced apart from the clamp assembly,
wherein the clamp assembly comprises a hinge and a first arcuate leg attached to the first clamp arm, the first arcuate leg positioned below the hinge and projects forward of the hinge behind the first clamp arm toward a medial portion of the first clamp arm and further comprises a second arcuate leg attached to the second clamp arm, the second arcuate leg positioned below the hinge and projects forward of the hinge behind the second clamp arm toward a medial portion of the second clamp arm, and wherein the first clamp arm and the second clamp arm define an open U-shape positioned laterally spaced apart from the hinge when the clamp assembly is in a closed position.

17. A cardiothoracic surgical device comprising:
a dual lumen cannula comprising a distal end portion configured to reside inside an aorta of a patient, wherein the distal end portion comprises an elongate body, wherein the elongate body comprises an outer wall, a closed distal tip and an internal wall inside the outer wall that extends across the elongate body in a longitudinal direction, wherein the elongate body comprises a first lumen positioned on one side of the internal wall with a first orifice extending through the outer wall and a second lumen on an opposing side of the internal wall with a second orifice extending through the outer wall, wherein the first lumen is in fluid isolation from the second lumen, and wherein the distal end portion further comprises a coupling pin that extends laterally outward of the elongate body at a position that is above and adjacent to the elongate body;
a clamp assembly that is detachably coupled to the coupling pin, the clamp assembly comprising a hinge with first and second clamp arms that are configured to pivot relative to the hinge between open and closed positions, wherein the hinge is above and laterally spaced apart from the first and second clamp arms, wherein, when coupled together, the elongate body remains in a fixed position relative to the clamp assembly, and wherein in the closed position, the first and second clamp arms are configured to close against the elongate body with a vessel wall of an aorta therebetween to thereby separate the aorta into two fluidly isolated compartments;
a first conduit that is attached to the first lumen and that is configured to extend outside the aorta, with a length sufficient to extend external to the patient; and a second conduit that is attached to the second lumen and that is configured to extend outside the aorta, with a length sufficient to extend external to the patient, wherein the clamp assembly comprises an aperture sized and configured to slidably receive the coupling pin to hold the clamp assembly in a fixed longitudinal position relative to the elongate body, and wherein the coupling pin extends laterally through the aperture so that a free end of the coupling pin is outside of the clamp assembly.

18. The cardiothoracic surgical device of claim 17, wherein, in position, the first orifice is configured to face a descending segment of the aorta and the second orifice is configured to face an ascending aorta segment of the aorta, wherein the first orifice has a first length with a center and the second orifice has a second length and a center, and wherein part of the first length is positioned along part of the second length at spaced apart positions of the elongate body with the center of the first orifice positioned above the center of the second orifice.

19. The cardiothoracic surgical device of claim 17, wherein the elongate body is a tubular body and the internal wall extends radially across and along an entire length of the tubular body between the first lumen and the second lumen.

20. The cardiothoracic surgical device of claim 17, wherein the elongate body has a proximal end that comprises a hub and that is configured to be external to the aorta, wherein the elongate body is below the hub and is configured to reside entirely in the aorta, and wherein the hub comprises a first branch in fluid communication with the first lumen and a second branch in fluid communication with the second lumen, wherein the first and second branches extend above the hub and terminate adjacent the hub, and wherein at least one of the first and second branches angle outward from a longitudinally extending centerline of the elongate body in an upward direction with the first branch connected to the first conduit and the second branch connected to the second conduit.

21. A cardiothoracic surgical device comprising:

a dual lumen cannula comprising a distal end portion configured to reside inside an aorta of a patient, wherein the distal end portion comprises an elongate body, wherein the elongate body comprises an outer wall, a closed distal tip and an internal wall inside the outer wall that extends across the elongate body in a longitudinal direction, wherein the elongate body comprises a first lumen positioned on one side of the internal wall with a first orifice extending through the outer wall and a second lumen on an opposing side of the internal wall with a second orifice extending through the outer wall, wherein the first lumen is in fluid isolation from the second lumen, and wherein the distal end portion further comprises a coupling pin that extends laterally outward of the elongate body at a position that is above and adjacent to the elongate body;

a clamp assembly that is detachably coupled to the coupling pin, the clamp assembly comprising a hinge with first and second clamp arms that are configured to pivot relative to the hinge between open and closed positions, wherein the hinge is above and laterally spaced apart from the first and second clamp arms, wherein, when coupled together, the elongate body remains in a fixed position relative to the clamp assembly, and wherein in the closed position, the first and second clamp arms are configured to close against the elongate body with a vessel wall of an aorta therebetween to thereby separate the aorta into two fluidly isolated compartments;

a first conduit that is attached to the first lumen and that is configured to extend outside the aorta, with a length sufficient to extend external to the patient; and a second conduit that is attached to the second lumen and that is configured to extend outside the aorta, with a length sufficient to extend external to the patient, wherein the clamp assembly comprises a first arcuate leg attached to the first clamp arm, the first arcuate leg positioned below the hinge and projects forward of the hinge behind the first clamp arm toward a medial portion of the first clamp arm and a second arcuate leg attached to the second clamp arm, the second arcuate leg positioned below the hinge and projects forward of the hinge behind the second clamp arm toward a medial portion of the second clamp arm, and wherein the first clamp arm and the second clamp arm define an open U-shape positioned laterally spaced apart from the hinge when the clamp assembly is in a closed position.

* * * * *